(12) United States Patent
Drexler et al.

(10) Patent No.: US 9,282,917 B2
(45) Date of Patent: Mar. 15, 2016

(54) SYSTEMS AND METHODS FOR A TINNITUS THERAPY

(71) Applicant: Otoharmonics Corporation, Portland, OR (US)

(72) Inventors: Daniel Drexler, Montevideo (UY); Michael Baker, Portland, OR (US); Marisa Pedemonte Benvenuto, Montevideo (UY); Dario Geisinger Yasky, Givat Shmuel (IL); Andres Bianco de Olea, Lomas de Solymar (UY)

(73) Assignee: Otoharmonics Corporation, Portland, OR (US)

( * ) Notice: Subject to any disclaimer, the term of this patent is extended or adjusted under 35 U.S.C. 154(b) by 1 day.

(21) Appl. No.: 14/317,333

(22) Filed: Jun. 27, 2014

(65) Prior Publication Data
US 2015/0003650 A1    Jan. 1, 2015

Related U.S. Application Data

(60) Provisional application No. 61/841,221, filed on Jun. 28, 2013, provisional application No. 61/841,254, filed on Jun. 28, 2013.

(51) Int. Cl.
*H04R 3/02* (2006.01)
*A61B 5/12* (2006.01)
*G06F 19/00* (2011.01)
*H03G 3/00* (2006.01)
*H04R 25/00* (2006.01)
*A61B 5/00* (2006.01)

(52) U.S. Cl.
CPC .............. *A61B 5/128* (2013.01); *A61B 5/4836* (2013.01); *G06F 19/3487* (2013.01); *H03G 3/00* (2013.01); *H04R 25/75* (2013.01); *A61B 5/0022* (2013.01)

(58) Field of Classification Search
CPC ....................................................... H04R 25/75
See application file for complete search history.

(56) References Cited

U.S. PATENT DOCUMENTS

| | | | |
|---|---|---|---|
| 5,403,262 A * | 4/1995 | Gooch | A61B 5/12 600/28 |
| 6,682,472 B1 | 1/2004 | Davis | |
| 7,081,085 B2 | 7/2006 | Viirre et al. | |
| 7,347,827 B2 | 3/2008 | Choy | |
| 7,572,234 B2 | 8/2009 | Viirre et al. | |
| 7,850,596 B2 | 12/2010 | Davis et al. | |

(Continued)

OTHER PUBLICATIONS

About—HushTinnitus, HushTinnitus, Available as early as Nov. 27, 2013, http://www.hushtinnitus.com/about?c2=SU&did=414764&au=383aabf96d04b8a2&ts=96059502.87#, 3 pages.

*Primary Examiner* — Curtis Kuntz
*Assistant Examiner* — Ryan Robinson
(74) *Attorney, Agent, or Firm* — Alleman Hall McCoy Russell & Tuttle LLP

(57) ABSTRACT

The treatment of tinnitus may include a tinnitus therapy including generating a tinnitus therapy sound that is similar to a patient's perceived tinnitus sound. In one example, a method for generating a tinnitus adjusted sound may include presenting a plurality of different sound templates to a user from a series of tinnitus therapy sound templates, receiving a selection by the user of one or more of the templates, receiving an adjustment to one or more of the selected templates, and generating a therapy sound based on the adjusted selections.

14 Claims, 22 Drawing Sheets

(56) References Cited

U.S. PATENT DOCUMENTS

| | | |
|---|---|---|
| 7,981,047 B2 | 7/2011 | Viirre et al. |
| 8,043,203 B2 * | 10/2011 | Park .................. A61F 11/00 381/312 |
| 8,098,859 B2 | 1/2012 | Zeng et al. |
| 8,185,383 B2 | 5/2012 | Zeng et al. |
| 8,273,034 B2 * | 9/2012 | Fogel .................. A61B 5/121 600/559 |
| 8,306,248 B2 | 11/2012 | DiGiovanni et al. |
| 8,357,102 B2 | 1/2013 | Zeng et al. |
| 8,608,638 B2 * | 12/2013 | McGuire ............ A61M 21/00 600/25 |
| 8,666,501 B2 | 3/2014 | Kilgard et al. |
| 2007/0203535 A1 | 8/2007 | Zeng et al. |
| 2009/0124850 A1 | 5/2009 | Moore et al. |
| 2009/0307590 A1 | 12/2009 | Frater et al. |
| 2010/0208631 A1 | 8/2010 | Zhang et al. |
| 2011/0054243 A1 | 3/2011 | Davis et al. |
| 2011/0071340 A1 | 3/2011 | McGuire |
| 2011/0245235 A1 | 10/2011 | Hanley et al. |
| 2012/0046713 A1 | 2/2012 | Hannemann et al. |
| 2012/0283593 A1 * | 11/2012 | Searchfield ........ A61M 21/00 600/559 |
| 2013/0039517 A1 | 2/2013 | Nielsen et al. |
| 2013/0204170 A1 | 8/2013 | Zeng et al. |
| 2013/0253258 A1 | 9/2013 | Davis et al. |

* cited by examiner

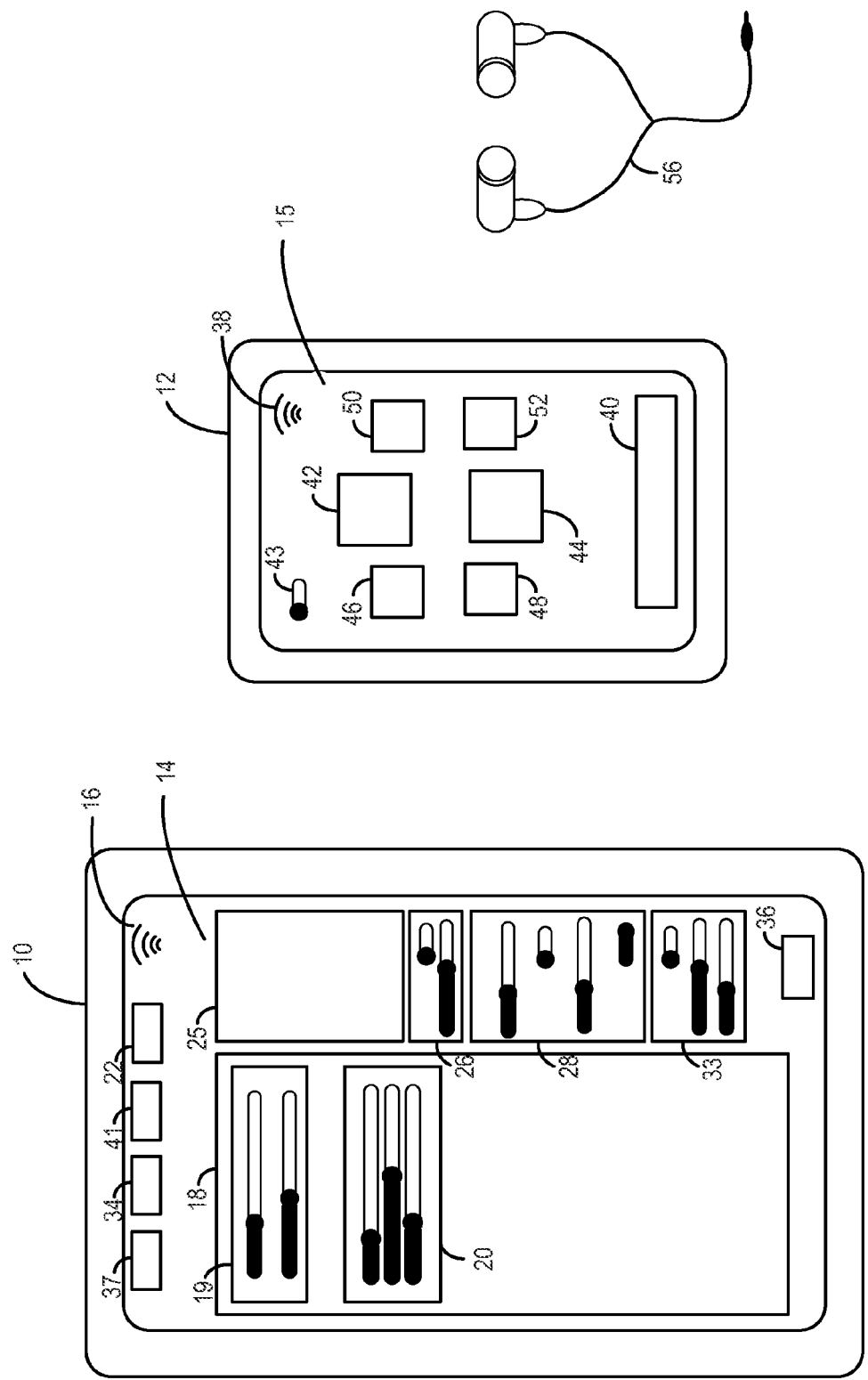

SYSTEMS AND METHODS FOR A TINNITUS THERAPY

PRIORITY CLAIM

This application claims priority to U.S. Provisional Application Nos. 61/841,221 and 61/841,254, filed Jun. 28, 2013, which are hereby incorporated by reference herein in their entirety.

BACKGROUND AND SUMMARY

Tinnitus is the sensation of hearing sounds when there are no external sounds present and can be loud enough to attenuate the perception of outside sounds. Tinnitus may be caused by inner ear cell damage resulting from injury, age-related hearing loss, and exposure to loud noises. The tinnitus sound perceived by the affected patient may be heard in one or both ears and also may include ringing, buzzing, clicking, and/or hissing.

Some methods of tinnitus treatment and/or therapy include producing a sound in order to mask the tinnitus of the patient. One example is shown by U.S. Pat. No. 7,850,596 where the masking treatment involves a pre-determined algorithm that modifies a sound similar to a patient's tinnitus sound.

However, the inventors herein have recognized issues with such approaches. For example, the modified sound used in the treatment is generated using a masking algorithm that only partially modifies the spectral qualities of the tinnitus sound. As such, the modified tinnitus sound includes the tinnitus sound of broad band noise only. Thus, an individual patient's tinnitus sound may not be completely masked by the modified tinnitus sound.

In one example approach, some of the above issues may be addressed by a method for generating a tinnitus adjusted sound, comprising presenting a plurality of different sound templates to a user from a series of tinnitus therapy sound templates, receiving a selection by the user of one or more of the templates, receiving an adjustment to one or more of the selected templates, and generating a therapy sound based on the adjusted selections.

In another example, a method for creating a tinnitus therapy may comprise presenting each of a pure tone, a white noise, and a combined tone tinnitus therapy sound template to a user, thereby generating a tinnitus therapy sound based on the tinnitus therapy sound template selected by the user. Further, the method may include adjusting the tinnitus therapy sound based on at least one of a frequency parameter and an intensity parameter selected by the user.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 1A-E show schematic diagrams of example devices for a tinnitus therapy including a healthcare professional's device and a patient's device.

DETAILED DESCRIPTION

Figure 2:
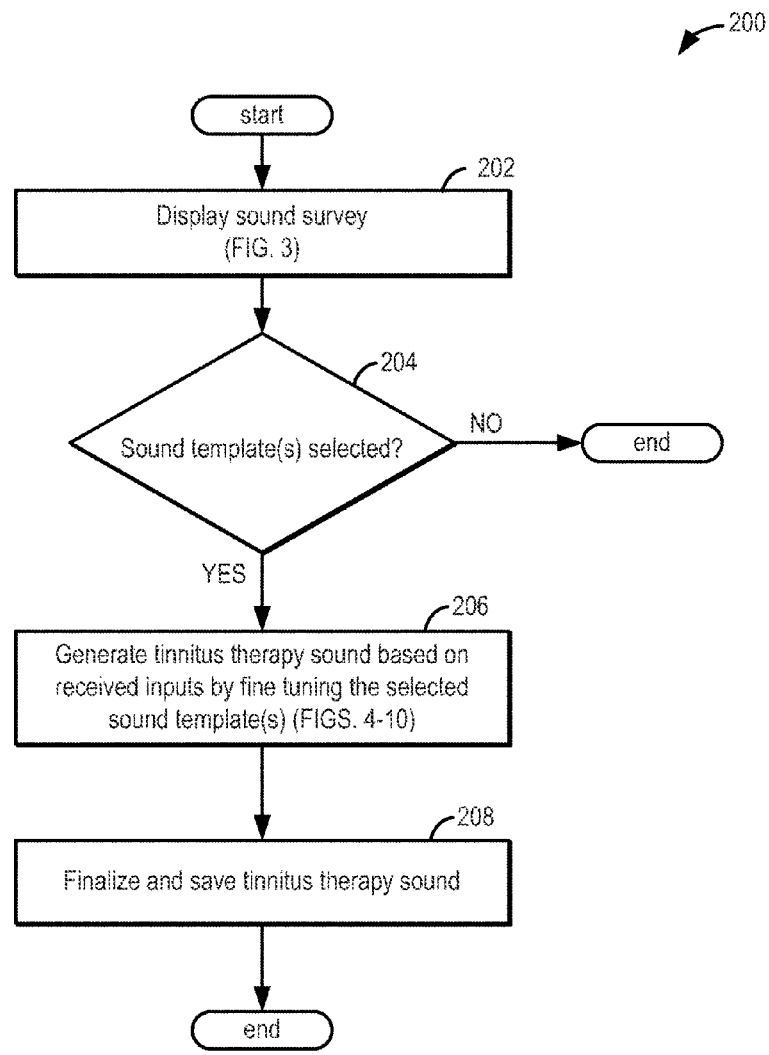
FIG. 2 shows an example method for generating a tinnitus therapy including a healthcare professional's device.
Figure 3A:
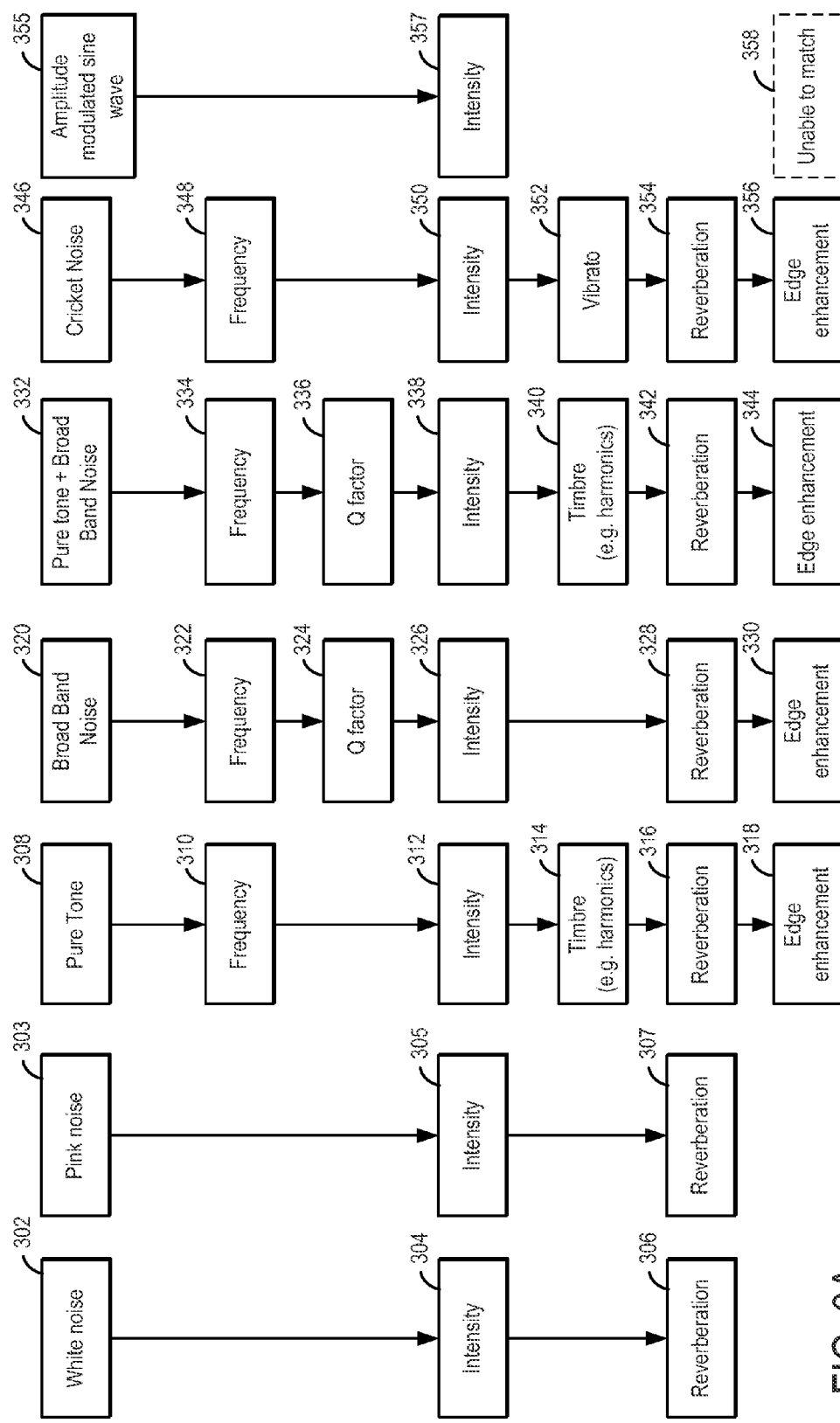
FIGS. 3A-D show example methods for generating a sound survey including adjusting default tinnitus therapy sound templates.
Figure 3B:
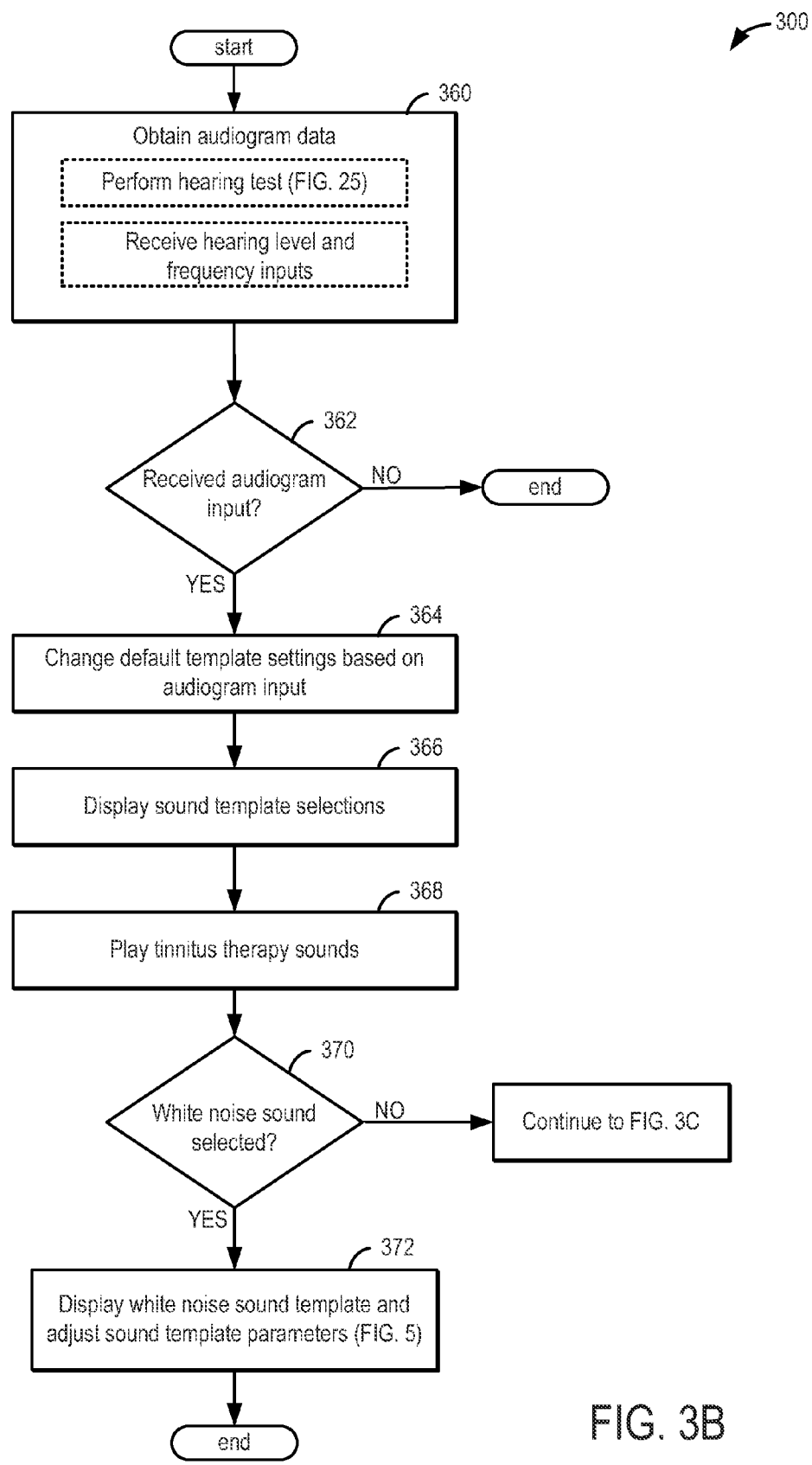
Figure 8:
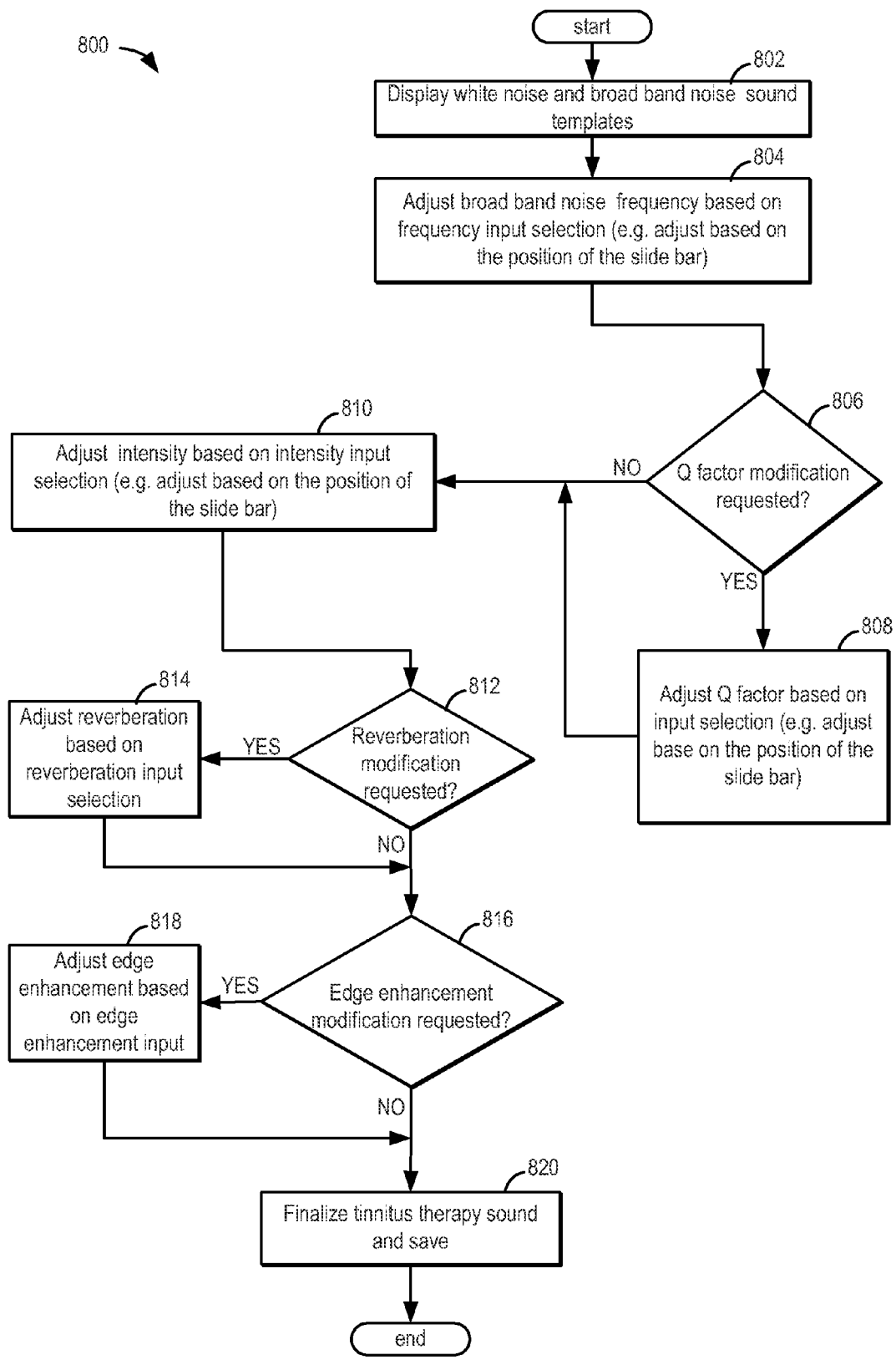
FIG. 8 shows an example method for generating a combination tinnitus therapy sound including both a white noise sound template and a broad band noise sound template.
Figure 9:
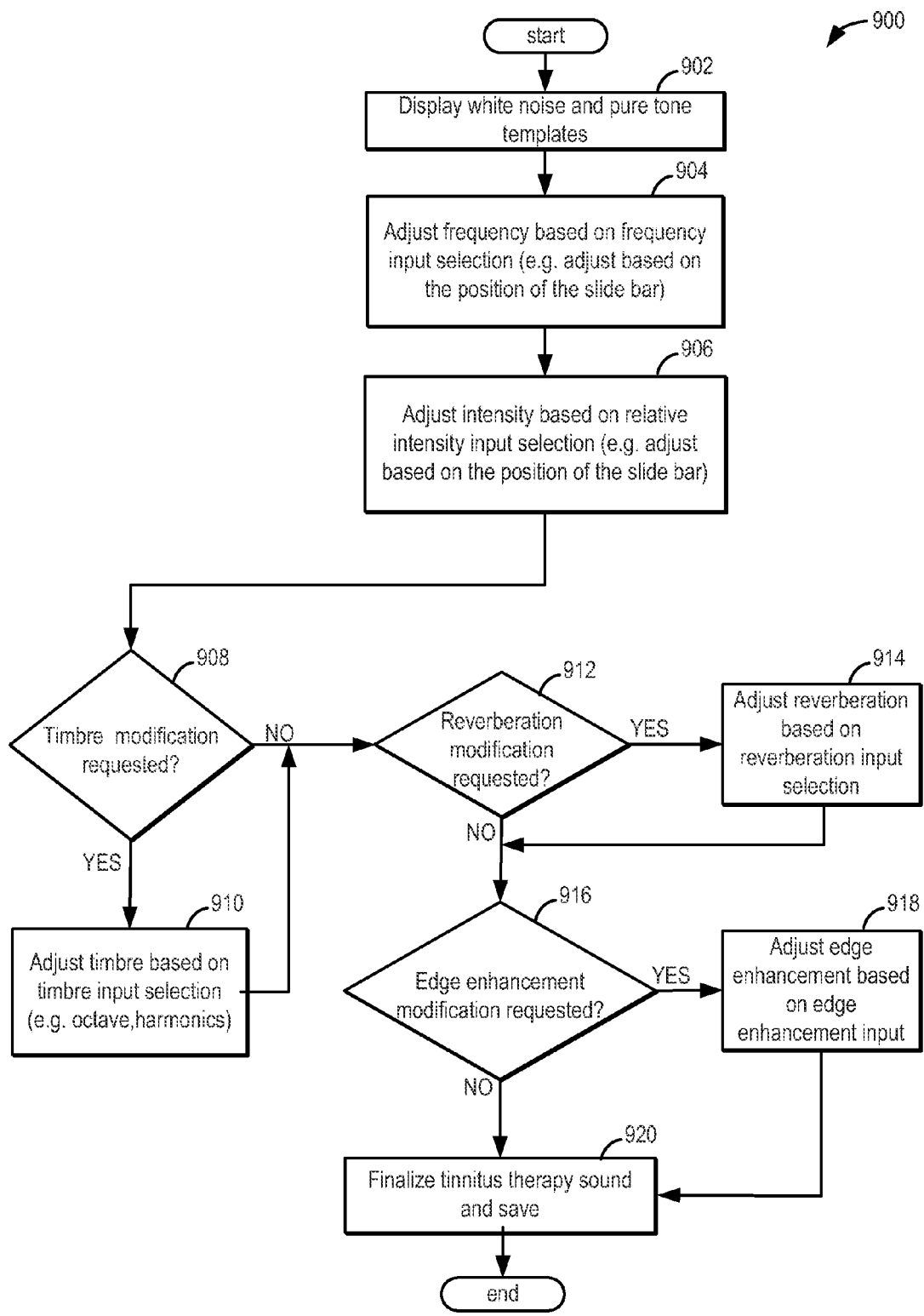
FIG. 9 shows an example method for generating a combination tinnitus therapy sound including both a white noise sound template and a pure tone sound template.
Figure 10:
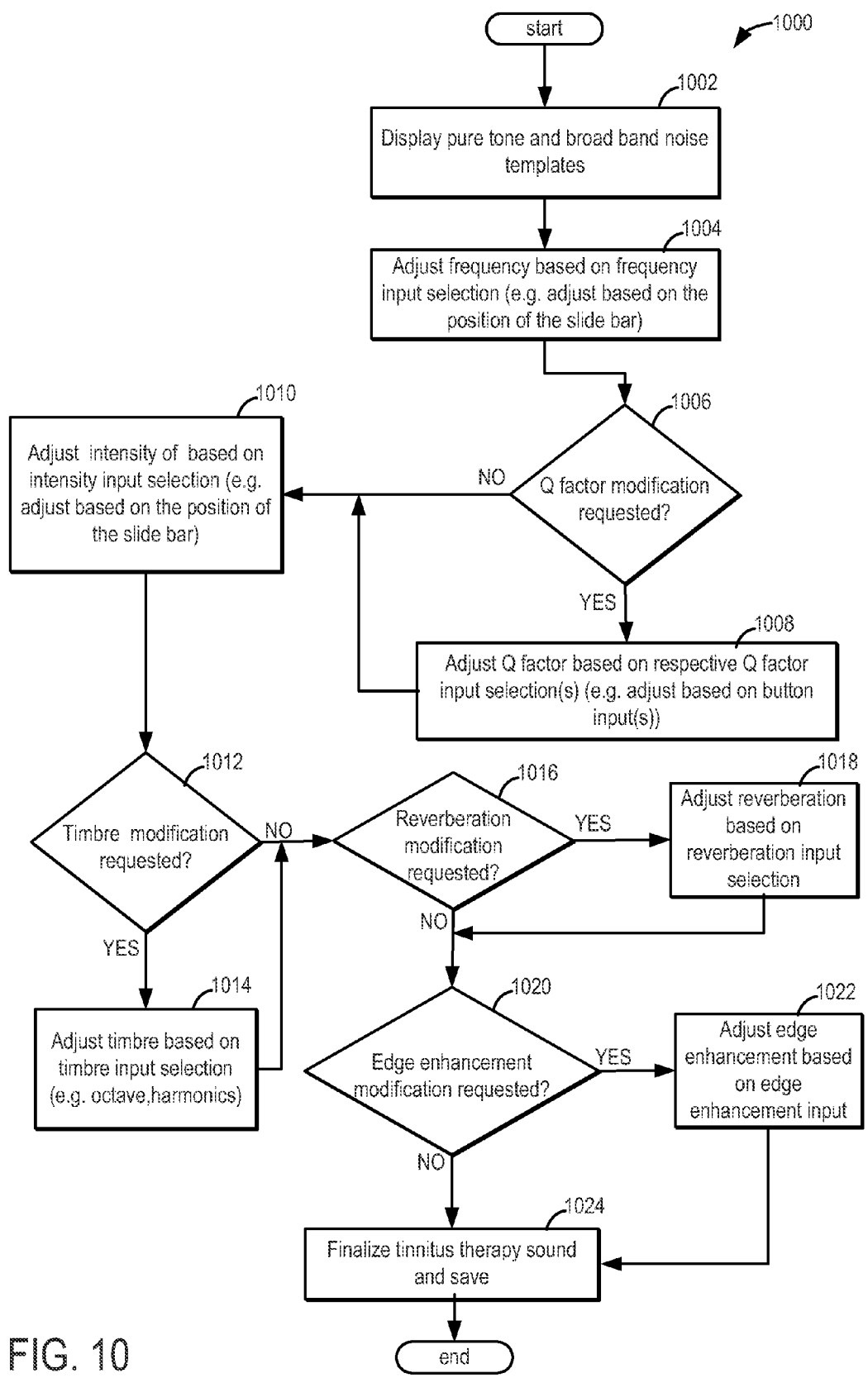
FIG. 10 shows an example method for generating a combination tinnitus therapy sound including both a pure tone sound template and a broad band noise sound template.
Figure 11:
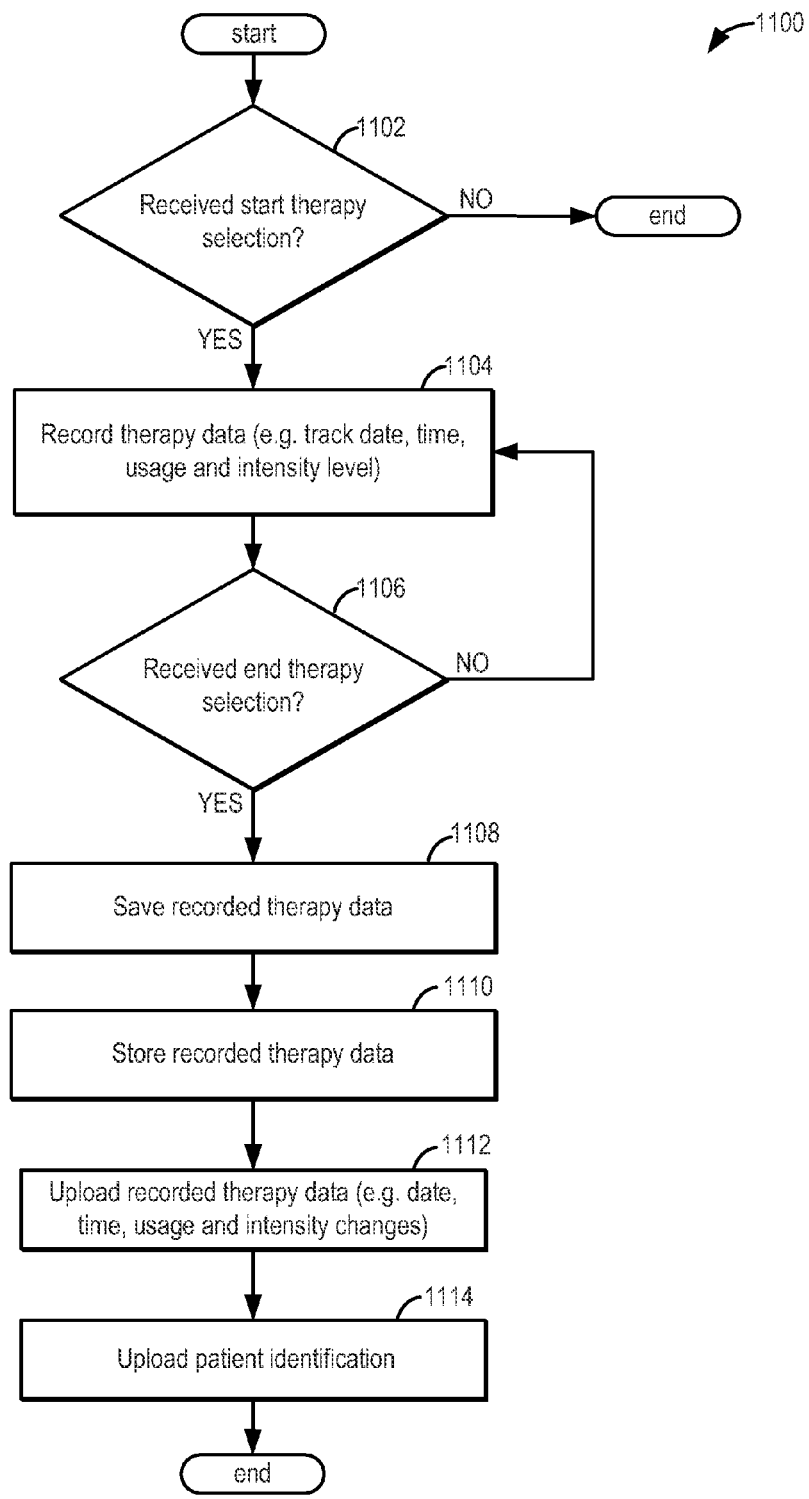
FIG. 11 shows an example method for tracking patient data.
Figure 12:
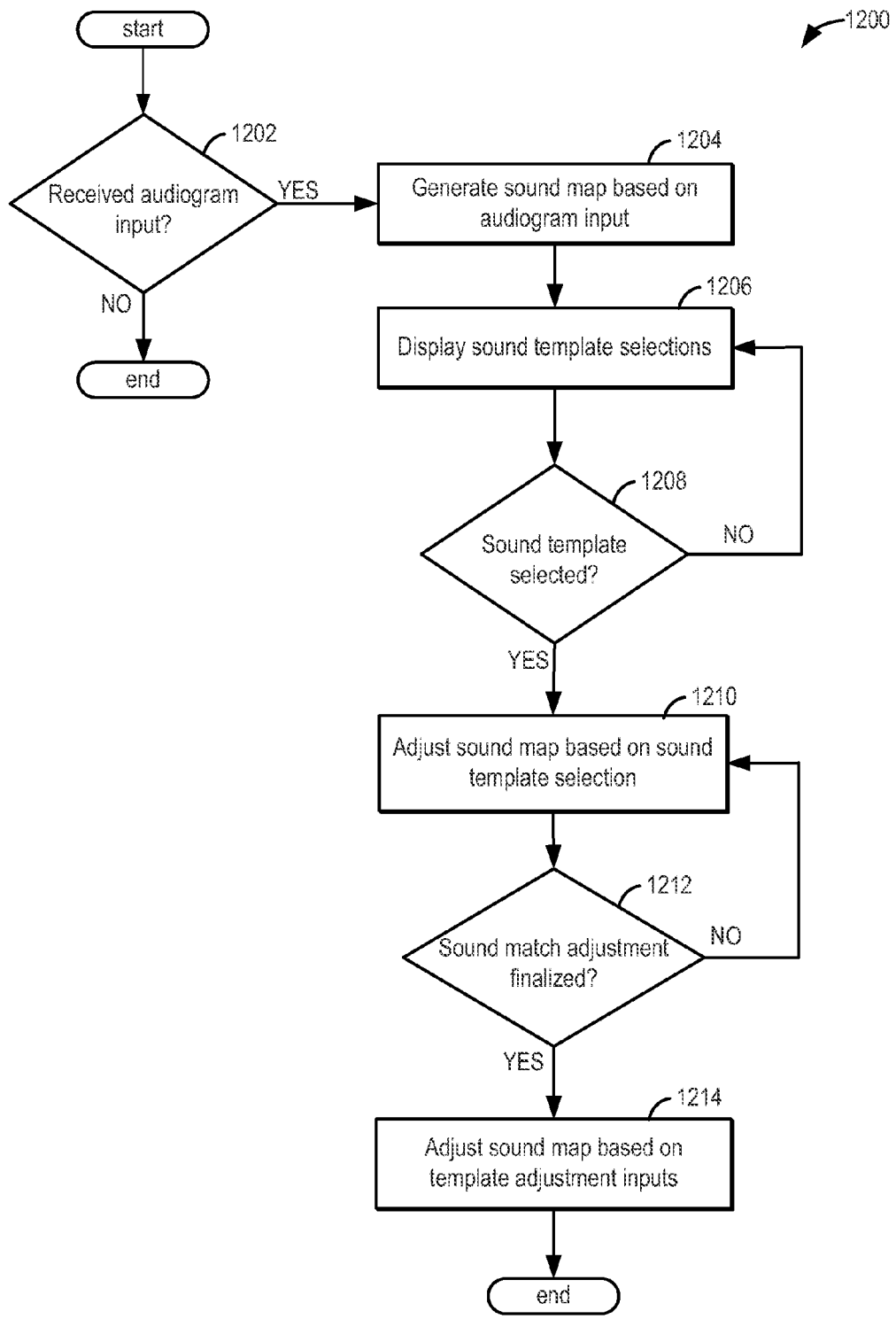
FIG. 12 shows an example method for generating a sound map.
Figure 25:
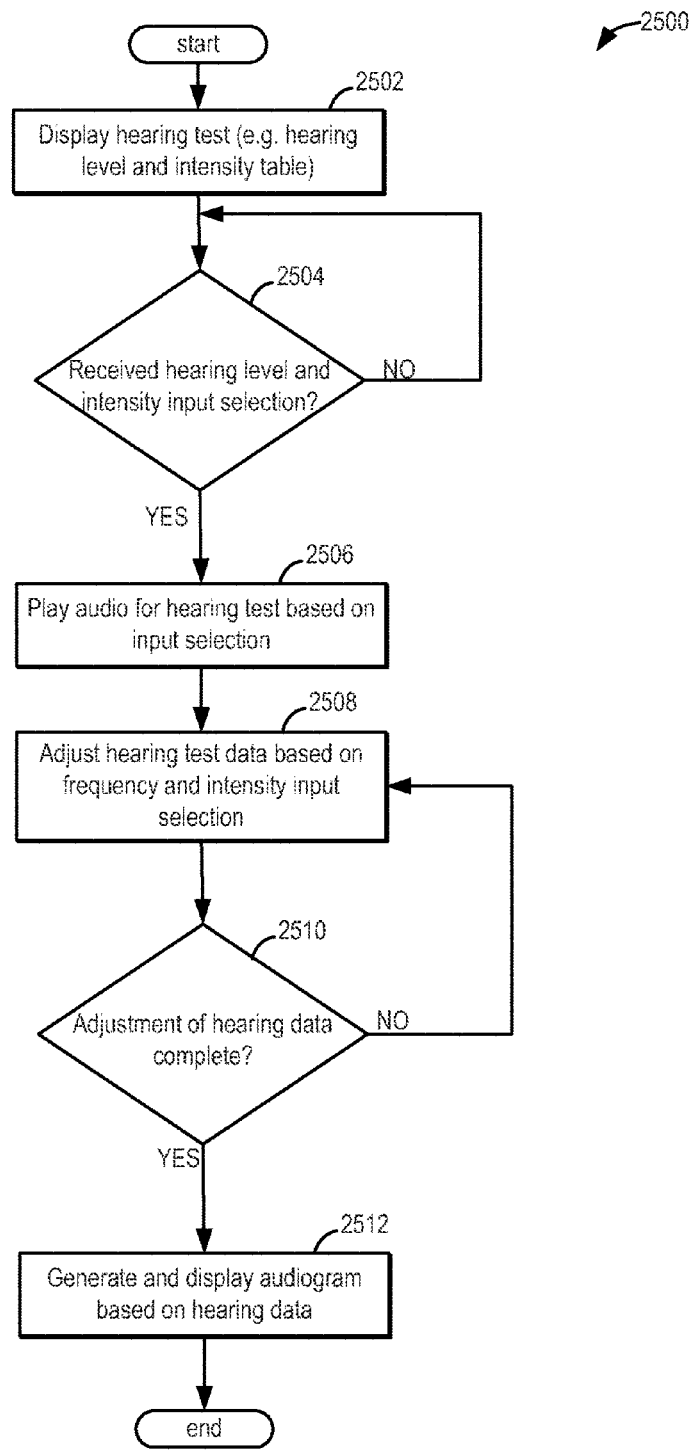
FIG. 25 shows an example method for generating an audiogram including performing a hearing test.

Methods and systems are provided for a tinnitus therapy for the treatment of tinnitus using a healthcare professional's device and a patient's device (FIGS. 1A-E). The healthcare professional's device may be used to generate the tinnitus therapy for an individual patient's perceived tinnitus. In addition, the patient's device may be used to deliver the tinnitus therapy to the individual patient over a set duration of time. The tinnitus therapy includes generating a tinnitus therapy sound in order to deliver a tinnitus sound that may be similar to the patient's perceived tinnitus (FIG. 2). Further, the tinnitus therapy includes generating a sound survey. Generating the sound survey may include inputting an individual patient's hearing threshold data from an audiogram, as well as selecting one or more specific tinnitus therapy sound templates that resemble the patient's perceived tinnitus (FIGS. 3A-B and 25). The tinnitus therapy may include adjusting the selected tinnitus therapy sound template(s). For example, the adjustments may include modifying the frequency, intensity, an octave input, a Q factor, reverberation, and/or white noise edge enhancement of the selected tinnitus therapy sound template(s) (FIGS. 4-7), but do not include adding further amplitude or frequency modulation. The adjustments made to the selected tinnitus therapy sound template(s) may be based on the type of sound (e.g., white noise, pink noise, broadband, cricket, pure tone, combined pure tone and broadband, or amplitude modulated sine wave) included in the selected tinnitus therapy sound template(s). Generating a tinnitus therapy sound may also include selecting more than one tinnitus therapy sound template as well as adjusting the selected individual tinnitus therapy sound templates. Then, the adjusted selected tinnitus therapy sound templates may be combined to generate one tinnitus therapy sound. The combination of two or more tinnitus therapy sound templates may result in a tinnitus therapy sound that resembles an individual patient's perceived tinnitus (FIGS. 8-10). Once a tinnitus therapy is generated, the sound therapy, including the generated tinnitus therapy sound, may be transferred from the healthcare professional's device to the patient's device. The patient's device may then present (e.g., play) the tinnitus therapy to the patient for a set duration of time. The patient's device may also record and track user input data during the duration of the tinnitus therapy. Specifically, patient information, dates, times, and user intensity levels may be recorded such that a physician may upload recorded data in order to track a patient's progress over time (FIG. 11). A tinnitus therapy may also include the generation of a sound map. In one example, the sound map may be a visual representation of an individual patient's perceived tinnitus. An audiogram, tinnitus therapy sound template selection, and tinnitus therapy sound may modify the sound map so that the sound map may be customized to an individual patient's perceived tinnitus (FIG. 12).

Referring to FIG. 1A, the figure shows a schematic diagram of example devices for a tinnitus therapy including healthcare professional's device 10 and patient's device 12. Healthcare professional's device 10 may be used and/or operated by a medical provider including, but not limited to, physicians, audiologists, nurses, and/or technicians. In another example, healthcare professional's device 10 may be used and/or operated by a patient. Thus, the user of the healthcare professional's device may be one or more of a patient or a medical provider. Further, the user of the patient's device may be the patient.

Healthcare professional's device 10 and patient's device 12 are physical, non-transitory devices configured to hold data and/or instructions executable by a logic subsystem. The logic subsystem may include individual components that are distributed throughout two or more devices, which may be remotely located and/or configured for coordinated processing. One or more aspects of the logic subsystem may be virtualized and executed by remotely accessible networked computing devices. Healthcare professional's device 10 and patient's device 12 may be configured to execute one or more instructions related to a tinnitus therapy. In addition, healthcare professional's device 10 and patient's device 12 may also include a user interface (e.g. display screens 14 and 15) for displaying information to the user and receiving digital information from the user, such as patient information and adjustments to the tinnitus therapy. In one example, the display screen(s) may be a touch screen. Information received from the user may be in various digital forms that represent a user's inputs. For example, the user may enter text, select, and/or move slide bars or other adjustable input buttons. In the example of the display screen being a touch screen, the user may adjust the input buttons through the touch screen. In another example, if the display screen is not a touch screen, the user may adjust the input buttons through a secondary device such as a computer mouse and/or keyboard. Further, healthcare professional's device 10 and patient's device 12 may generate tinnitus therapy sound templates and tinnitus therapy sounds to transmit the automatically generated electronic tinnitus therapy to the user. In one example, healthcare professional's device 10 and patient's device 12 may interact via a wired or wireless network which may allow for bidirectional communication between the devices. In another example, a patient's device 12 may track and/or record tinnitus therapy data, including metadata, that may be transmitted to the healthcare professional's device 10. In another example, recorded and/or stored therapy data may be written in an HTML5 format such that the transferred data, via a remote portal, may be received on a secured webpage.

Figure 1D:
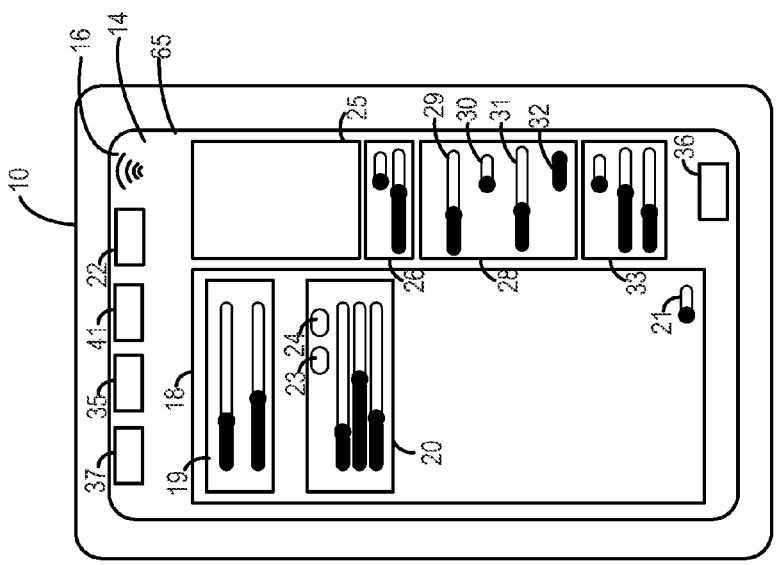

Continuing with FIG. 1A, display screen 14 of healthcare professional's device 10 may include a plurality of input buttons for selecting sound parameters, such as frequency, intensity, octaves, Q factor, reverberation, and/or white noise edge enhancement. Further, display screen 14 may display different combinations of input buttons and graphics based on a selected user interface. Additional details and examples of sample user interfaces are presented below with reference to FIGS. 1B-1E.

In the example shown in FIG. 1A, display screen 14 includes controls for generating a tinnitus therapy sound. The tinnitus therapy sound generated with the methods described below may also be referred to herein as a tinnitus sound match or a tinnitus therapy sound match. The controls used for generating the tinnitus sound match include tinnitus sound match input button 37, generating a tinnitus therapy via therapy input button 34, copying a tinnitus sound match via copy tinnitus sound match input button 41, and adding a template to the tinnitus therapy via add template input button 22 (see also FIGS. 1B-D). The tinnitus therapy sound may be generated based on adjustments to pre-defined tinnitus therapy templates, the pre-defined tinnitus therapy templates including a tinnitus therapy sound or combination of sounds (e.g., cricket noise, broad band noise, pure tone and broad band noise, etc.) within certain frequency and intensity ranges. The pre-defined tinnitus therapy templates may be modified by patient-specific hearing threshold data such that the tinnitus therapy sound template includes a tinnitus therapy sound audible to the patient.

Figure 1C:
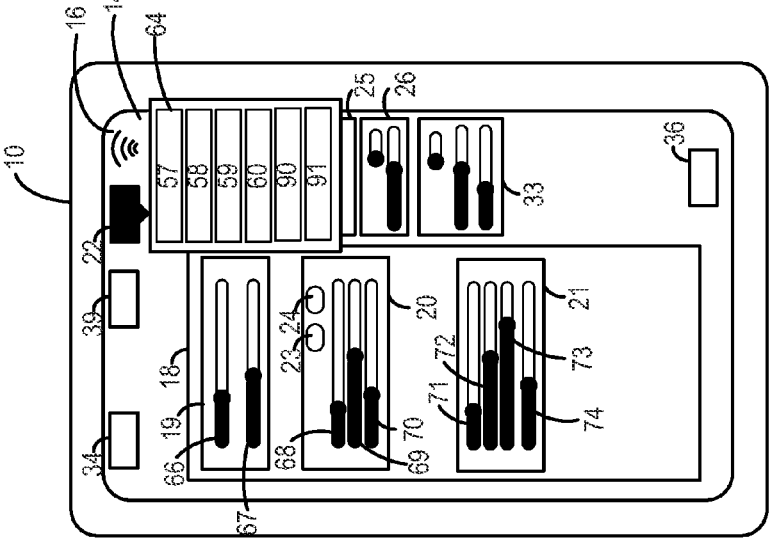

In one example, once a tinnitus therapy sound template is selected, specific tinnitus therapy sound template displays may be displayed in tinnitus therapy sound display 18 (e.g., sound list) which may include a first tinnitus therapy sound template display 19 and a second tinnitus therapy sound template display 20 in order to generate a specific tinnitus therapy, or tinnitus therapy sound (see also FIG. 1C). Each tinnitus therapy sound template display may include a specific tinnitus therapy sound template (e.g., cricket noise, broad band noise, etc.), along with various input buttons to adjust sound parameters of the tinnitus therapy sound template. In one example, a first tinnitus therapy sound template display 19 and a second tinnitus therapy sound template display 20 may include a cricket noise sound template, a white noise sound template, a pure tone sound template, and/or a broad band noise sound template. In addition, a tinnitus therapy sound template display may include a set of controls and/or adjustments for modifying the sound characteristics of the tinnitus therapy sound template. The controls and/or adjustments may include a volume adjustment (e.g. intensity adjustment), a frequency adjustment (e.g., pitch adjustment), a timbre adjustment, a Q factor adjustment, a vibrato adjustment, a reverberation adjustment, and/or a white noise edge enhancement adjustment. As such, the controls and/or adjustments of a template may include an input button and/or slide bar input.

Display screen 14 may also include a session notes window 25 that includes a space to input notes about a tinnitus therapy. Notes written in the session notes window 25 may be displayed as part of the tinnitus therapy. Further, a sound monitor 26 adjusts the volume of the healthcare professional's device. In one example, sound monitor 26 generates a sound output in order for the tinnitus therapy sound match to be monitored via an external speaker of the healthcare professional's device 10 (not shown).

Display screen 14 may include a therapy parameter window 28. In one example, therapy parameter window 28 may also include a help-to-sleep option, a changing volume option, and a maximum duration option. The additional features of the therapy parameter window 28 are described further below with regard to FIG. 1D. Further, a sound option 33 enables the physician to allow adjustment of the volume of the generated tinnitus sound match on a patient's device 12. For example, when sound option 33 is activated, a patient is able to adjust his/her tinnitus therapy volume during the duration of the tinnitus therapy treatment.

In order to complete the tinnitus therapy, when selected, an end session input button 36, or similar input button, saves the tinnitus therapy to healthcare professional's device 10. A wireless input 16 sends the tinnitus therapy to a patient's device 12. In one example, once the therapy is completed and the session ends, a patient's device 12 is connected to healthcare professional's device 10 and the tinnitus therapy is loaded onto patient's device 12. In another example, after completing the tinnitus therapy on the healthcare professional's device 10, the completed tinnitus therapy (or tinnitus therapy sound) may be e-mailed over a secure network which may then be accessed via an internet connection on the patient's device 12. In yet another example, the competed tinnitus therapy sound may be transferred between the healthcare professional's device 10 and the patient's device 12 by bidirectional communication via a wired connection or a portable storage device.

Patient's device 12 may include a set of customized earphones 56. In one example, the earphones 56 are made from medical grade silicon and are custom molded and handcrafted to a patient's ears. Further, earphones 56 may be used while generating a tinnitus therapy via a healthcare professional's device as well as during the tinnitus therapy via the patient's device. In another example, another type of earphones or listening device may be used during generating the tinnitus therapy and during listening to the generated tinnitus therapy (e.g., tinnitus sound match). In some examples, a different set of earphones may be used while generating the tinnitus therapy via the healthcare professional's device 10 than when listening to the generated tinnitus therapy via the patient's device 12.

In another example, patient's device 12 can be used for either day or night treatment. If a night treatment is selected, a user interface may include a display screen 15 including a help-to-sleep input 43, and a wireless input 38. When selected, the help-to-sleep option plays a pre-determined sound (e.g. music). The pre-determined sound is separate from the tinnitus therapy, the tinnitus therapy including the tinnitus therapy sound match. Further, the pre-determined sound may be played for a pre-determined amount of time (e.g. 1-60 minutes).

When the allow changing volume option from the therapy parameter window 28 on healthcare professional's device 10 is selected as part of the tinnitus therapy, the patient's device 12 includes a user interface that may have a volume adjustment inputs 42 and 44 on display screen 15. In one example, display screen 15 may have volume adjustment inputs 46 and 48 for the left ear and volume adjustment inputs 50 and 52 for the right ear. Volume adjustment inputs 46, 48, 50, and 52 may be adjusted independently from volume adjustment inputs 42 and 44. In another example, the volume can be adjusted following the selection of the help-to-sleep option using volume adjustment inputs 46, 48, 50, and 52, as well as volume adjustment inputs 42 and 44. In another example, volume adjustment input 42 may increase the volume of the tinnitus sound match where as volume adjustment 44 may decrease the volume of the tinnitus sound match when selected. Further, volume adjustment inputs 46 and 50 may increase the volume of the left ear and right ear inputs, respectively. Conversely, volume adjustment inputs 48 and 52 may decrease the volume of the left ear and right ear inputs, respectively.

In order to start a tinnitus therapy, a user interface may include a display screen 15 including a start therapy input button 40. In this example, the pre-defined tinnitus therapy from healthcare professional's device 10 will begin once the start therapy input 40 is selected. The tinnitus therapy will play for a set duration of time based on the input from the therapy parameter window 28 on healthcare professional's device 10. For example, the tinnitus sound match created for the tinnitus therapy may play repeatedly without breaks for the designated duration of time. The start therapy input 40 may also be selected during a tinnitus therapy session in order to pause the therapy.

Figure 1B:
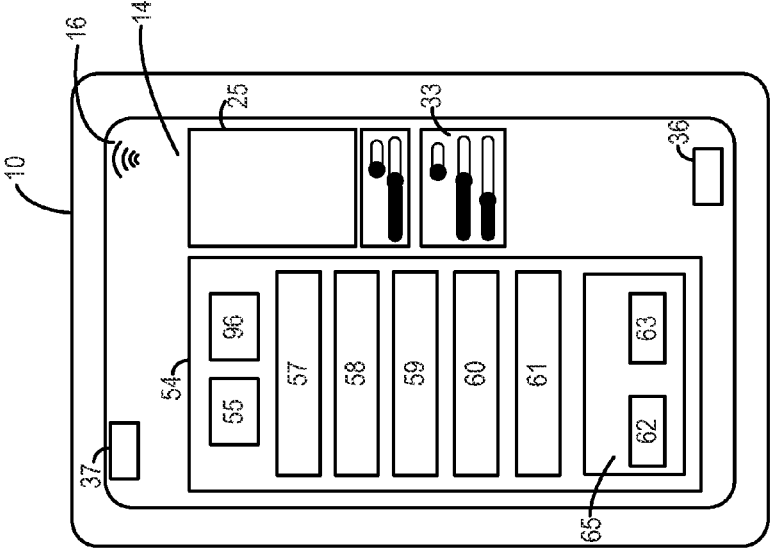

FIGS. 1B-D show schematic diagrams of a healthcare professional's device including example user interfaces. In particular, FIG. 1B shows a sample tinnitus sound template selection display, FIG. 1C shows a sample tinnitus sound display (e.g., tinnitus sound match display), and FIG. 1D shows a sample therapy display, as explained above and shown at FIG. 1A. In one example, generating a tinnitus therapy involves selecting the appropriate tinnitus therapy sound template, generating a tinnitus therapy sound based on adjustments of the tinnitus therapy sound template, and choosing specific therapy parameters.

Now referring to FIG. 1B, a healthcare professional's device 10 may include a user interface that may include a plurality of tinnitus therapy sound template selections or displays which may be used to generate a tinnitus therapy sound. In this example, display screen 14 includes a tinnitus therapy sound template selection display 54. A tinnitus therapy sound template selection display 54 includes audiogram inputs including a hearing level input 55 and a frequency input 96. In one example, when a hearing level input 55 and a frequency input 96 are selected, a user interface may prompt a user to input hearing threshold data (e.g. intensity and frequency thresholds). In another example, tinnitus therapy sound template selection display 54 may include a hearing test including a user generated audiogram. Specifically, a user interface may prompt a user to perform a hearing test. Upon completion of the hearing test, an audiogram may be generated based on user inputs. Based on the generated audiogram, a user interface may prompt a user to input the hearing threshold data into hearing level input 55 and frequency input 96. In another example, hearing threshold data from the generated audiogram may automatically fill into the hearing level input 55 and/or the frequency input 96 without further input from the user. In addition, tinnitus therapy sound template selection display 54 includes controls for selecting a plurality of tinnitus therapy sound templates. The tinnitus therapy sound template controls may include cricket noise sound template 57, white noise sound template 58, pure tone sound template 59, broad band noise sound template 60, a combination pure tone and broad band noise sound template 61, pink noise sound template 90, and amplitude modulated sine wave template 91. In an alternate example, the tinnitus therapy sound template controls (e.g., sound type options) may include cricket noise sound template 57, white noise sound template 58, pure tone sound template 59, broad band noise sound template 60, pink noise sound template 90, and amplitude (or frequency) modulated sine wave template 91.

In one example, when a tinnitus therapy sound template is selected (e.g., one of sound templates 57-61 and 90-91), a pre-defined tinnitus therapy sound template may be played and heard from an external speaker (not shown). For example, a pre-defined tinnitus therapy sound template may be generated and/or modified based on the hearing threshold data of an individual patient's audiogram. Following selection of a tinnitus therapy sound template, a user interface may prompt a user to confirm the tinnitus therapy sound template selection via display 65. Display 65 includes verification inputs 62 and 63, that when selected, confirm if the tinnitus therapy sound template selected is the correct template to be used for the tinnitus therapy. For example, if cricket noise sound template 57 is selected and the cricket noise played is similar to the patient's perceived tinnitus, then input 62 is selected. Conversely, if the cricket noise sound template played is not similar to the patient's perceived tinnitus, then input 63 is selected. Display screen 14 also includes a tinnitus therapy sound match input button 37. When the tinnitus therapy sound match input button 37 is selected, a user interface may include a tinnitus therapy sound display, as described further below with regard to FIG. 1C.

Now referring to FIG. 1C, in this example, display screen 14 of healthcare professional's device 10 includes a user interface including a tinnitus sound display (e.g., tinnitus sound match refinement display). As such, display screen 14 may include a tinnitus therapy sound display 18 including a first tinnitus therapy sound template display 19 and a second tinnitus therapy sound template display 20. In one example, the tinnitus therapy sound template or combination of tinnitus therapy sound templates displayed on the tinnitus therapy sound display 18 may be those selected from the tinnitus therapy sound template selection display 54. As such, tinnitus therapy sound display 18 may include one or more selected tinnitus therapy sound template displays including a cricket noise sound template display, a white noise sound template display, a pink noise sound template display, a pure tone sound template display, a broad band noise template display, an amplitude modulated sine wave template (e.g., amplitude modulated sound wave template) and/or a combination pure tone and broad band noise sound template display. In this example, first tinnitus therapy sound template 19 may be a white noise sound template display and second tinnitus therapy sound template 20 may be a pure tone sound template display. In other examples, tinnitus therapy sound display 18 may include other tinnitus therapy sound template display combinations such as a white noise sound template display combined with a broad band noise sound template display. In another example, a pure tone sound template display may be combined with a broad band noise sound template display. In one example, tinnitus therapy sound template display 19 includes volume adjustment inputs 66 and 67 for both left and right ears, respectively (e.g. a white noise sound template). In another example, tinnitus therapy sound template display 20 includes volume adjustment inputs 68 and 69 for both left and right ears, respectively, an adjustment input for frequency 70, and octave adjustment inputs 23 and 24 (e.g. a pure tone sound template). In another example, tinnitus therapy sound display 18 may include tinnitus therapy sound template display 21 for a broad band noise sound template which may include volume adjustment inputs 71 and 72 for both left and right ears, an adjustment for frequency input 73, and an adjustment for Q-factor input 74. Further, a cricket noise sound template display may include adjustment inputs for both left and right ears and an adjustment input for frequency. In another example, tinnitus therapy sound template displays may include a vibrato adjustment, reverberation adjustment, and/or a white noise edge enhancement adjustment.

After adjusting the tinnitus therapy sound templates via the tinnitus therapy sound template displays, additional tinnitus therapy sound template displays may be added to tinnitus therapy sound match display 18. By selecting the add template input button 22, a user interface may prompt a user to select an additional tinnitus therapy sound template display from tinnitus therapy sound template display 64. Tinnitus therapy sound template display 64 includes a plurality of tinnitus therapy sound templates including cricket noise sound template 57, white noise sound template 58, pure tone sound template 59, broad band noise sound template 60, a combination pure tone and broad band noise sound template, pink noise sound template 90, and amplitude modulated sine wave template 91. In alternate embodiments, the tinnitus therapy sound template display 64 may include a different combination of cricket noise sound template 57, white noise sound template 58, pure tone sound template 59, broad band noise sound template 60, a combination pure tone and broad band noise sound template, pink noise sound template 90, and amplitude modulated sine wave template 91. For example, the tinnitus therapy sound template display 64 may include cricket noise sound template 57, white noise sound template 58, pure tone sound template 59, broad band noise sound template 60, and pink noise sound template 90. In yet another example, the tinnitus therapy sound template display 64 may include white noise sound template 58, pure tone sound template 59, and a combined tone sound template, the combined tone tinnitus sound template including the combination pure tone and broad band noise sound template. Once a tinnitus therapy sound template is selected, the tinnitus therapy sound template display may be displayed in tinnitus therapy sound display 18 where the template(s) may then be adjusted.

Display screen 14 of healthcare professional's device 10 including the tinnitus therapy sound display 18, may include controls for selecting a therapy display via therapy input button 34 and loading a previously generated and saved tinnitus sound via load match input button 39. Following the conclusion of the tinnitus therapy sound process, a therapy input button 34 may be selected and a user interface may include a tinnitus therapy including therapy parameter window 28 as described further below with regard to FIG. 1D. Further, before adjusting the tinnitus therapy sound templates displayed in tinnitus therapy sound display 18, a load tinnitus sound match input button may be selected and a user interface may include the previously adjusted tinnitus sound template in the tinnitus therapy sound display 18.

Referring now to FIG. 1D, in this example, display screen 14 of healthcare professional's device 10 shows an example tinnitus therapy screen. Display screen 14 includes a therapy parameter window 28. In one example, therapy parameter window 28 includes the help-to-sleep option 30, allow changing volume option 32, and maximum duration input 29. The help-to-sleep option delays the start of the tinnitus therapy for use during night therapy. The help-to-sleep option includes a timeout option 31 that adjusts the time in which the help-to-sleep feature is active (e.g. 1-60 minutes). The allow changing volume option 32 enables modification of the tinnitus sound volume during therapy. However, if this option is turned off, the volume will stay as established by the physician (or other user) during the generation of the tinnitus therapy. The therapy parameter window 28 may also include a maximum duration input 29 that sets a maximum time duration for playing the tinnitus therapy (e.g. 1-8 hours).

Further, display screen 14 may include controls for generating a tinnitus therapy sound match via tinnitus sound match input button 37, loading a previously generated tinnitus therapy via a tinnitus therapy input button 35, copying a tinnitus therapy sound match via copy tinnitus sound match input button 41, and adding a template via add template input button 22. For example, before adjusting the therapy parameters, tinnitus therapy input button 35 may be selected and a graphical user interface will display a previously adjusted tinnitus therapy in therapy parameter window 28. The therapy input button may be selected if no modifications to the therapy parameters are required. Following the selection of the therapy parameters for the tinnitus therapy, a tinnitus match input button 37 may be selected and a user interface may include a tinnitus match display including previously selected tinnitus sound templates. A match input button 37 may be selected, for example, if further modifications to the tinnitus therapy sound templates need to be made before finalizing the tinnitus therapy.

Figure 1E:
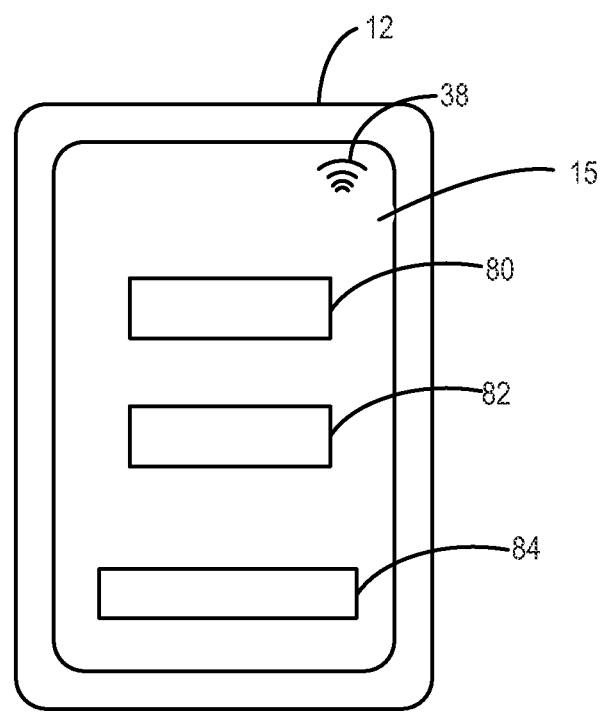

FIG. 1E shows a schematic diagram of another example user interface of the patient's device 12. Specifically, the display screen 15 shown in FIG. 1E shows a therapy selection screen. The display screen includes a sleep input button 80, an awake input button 82, and an appointment button 84. As described above, a user or patient may use the patient's device in sleep or awake mode. A healthcare professional may instruct the patient as to which therapy mode to use when assigning a tinnitus therapy protocol. Additionally, the appointment button 84 allows the patient's device 12 to be connected (e.g., wirelessly connected) with the healthcare professional's device 10 in order to generate, analyze, and/or adjust a tinnitus therapy. Thus, the display screen 15 shown in FIG. 1E may be an initial screen viewed by the patient before either starting the tinnitus therapy or connecting to a healthcare professional's device to create and/or adjust the tinnitus therapy.

As described above, the system of FIGS. 1A-E provide for a tinnitus therapy system, comprising one or more physical, non-transitory, devices configured to hold data and/or instructions executable by a logic subsystem to generate a tinnitus therapy sound based on a tinnitus therapy sound type selected by a user from a set of pre-defined tinnitus therapy sound templates. The generated tinnitus therapy sound may further be based on one or more of an intensity and frequency level of the selected tinnitus therapy sound template selected by the user. In one example, a first physical, non-transitory, device of the one or more physical, non-transitory, devices includes a user interface, such that the user interface includes a plurality of input buttons for selecting sound parameters. Additionally, the data and/or instructions are further executable to receive a patient's audiogram data, and to send the generated tinnitus therapy sound to a second physical, non-transitory, device of the one or more physical, non-transitory, devices. In an additional example, the second physical, non-transitory, device includes one or more intensity controls for adjusting an intensity of the generated tinnitus therapy sound. Further, the data and/or instructions on the second physical, non-transitory, device are executable to play the generated tinnitus therapy sound repeatedly without breaks and track intensity adjustments to the generated tinnitus therapy sound over time.

FIG. 2 shows an example method 200 for generating a tinnitus therapy using instructions stored on and executed by a logic subsystem of a healthcare professional's device, as explained with regard to FIGS. 1A-D. For example, a healthcare professional's device may include tinnitus sound templates, the tinnitus sound templates including tinnitus therapy sound types, in order to generate a tinnitus therapy sound (e.g., tinnitus sound match). As such, the healthcare professional's device may be used to generate a tinnitus therapy based on the selected tinnitus therapy sound templates and adjustments made to the selected tinnitus therapy sound templates and/or the tinnitus therapy sound.

The method 200 begins at 202 where a sound survey is displayed. The method at 202 may further include completing the sound survey. In one example, completing the sound survey may include receiving inputs via inputs (e.g., adjustment buttons) displayed on the user interface via the display screen. For example, the sound survey may include a hearing threshold data input and the selection of sound templates. In another example, the sound survey may include a hearing test. The hearing test may include generating an audiogram based on the hearing test data. The method at 202 for completing the sound survey is shown in further detail at FIGS. 3A-B. In one example, the tinnitus sound templates may include two or more of a cricket noise sound template, a white noise sound template, a pink noise sound template, a pure tone sound template, a broad band noise sound template, an amplitude modulated sine wave template, and a combination pure tone and broad band noise sound template. In an additional example, the sound templates selected may be a combination of at least two tinnitus therapy sound templates.

At 204, the method includes determining if the tinnitus sound template(s) have been selected. Once the template(s) are selected, at 206, a tinnitus therapy sound may be generated based on the sound survey and adjustments made to the frequency and intensity inputs. Herein, a tinnitus therapy sound may also be referred to as a tinnitus therapy sound match and/or tinnitus sound match. Methods for adjusting each tinnitus sound template (e.g. for each tinnitus sound type) are shown at FIGS. 4-8, described further below. For example, generating a tinnitus sound may include adjusting firstly a white noise sound template and secondly a pure tone sound template. Once the adjustments are made, the tinnitus sound templates are combined to make a specific tinnitus therapy sound. In another example, generating a tinnitus therapy sound may include adjusting firstly a white noise sound template and secondly a broad band noise sound template. In an additional example, generating a tinnitus sound match may include adjusting firstly a pure tone sound template and secondly a broad band noise sound template. Further, therapy parameters may be added to the tinnitus therapy sound to finalize the tinnitus therapy sound. In one example, therapy parameters may include adding a help-to-sleep feature, setting the maximum duration of the tinnitus therapy, and allowing a user to adjust the volume during the tinnitus therapy. At 208, the tinnitus therapy sound may be saved and finalized. Once the tinnitus therapy sound is finalized, the tinnitus therapy is complete and may be sent to the patient's device. In one example, the healthcare professional's device is configured to hold instructions executable to send the generated tinnitus therapy sound to a second physical, non-transitory device (e.g. the patient's device). In another example, finalizing the tinnitus therapy sound includes assigning the generated tinnitus therapy sound to an individual patient of the individual patient audiogram. Assigning the tinnitus therapy sound also includes storing the generated tinnitus therapy sound with a code corresponding to the individual patient.

Figure 3C:
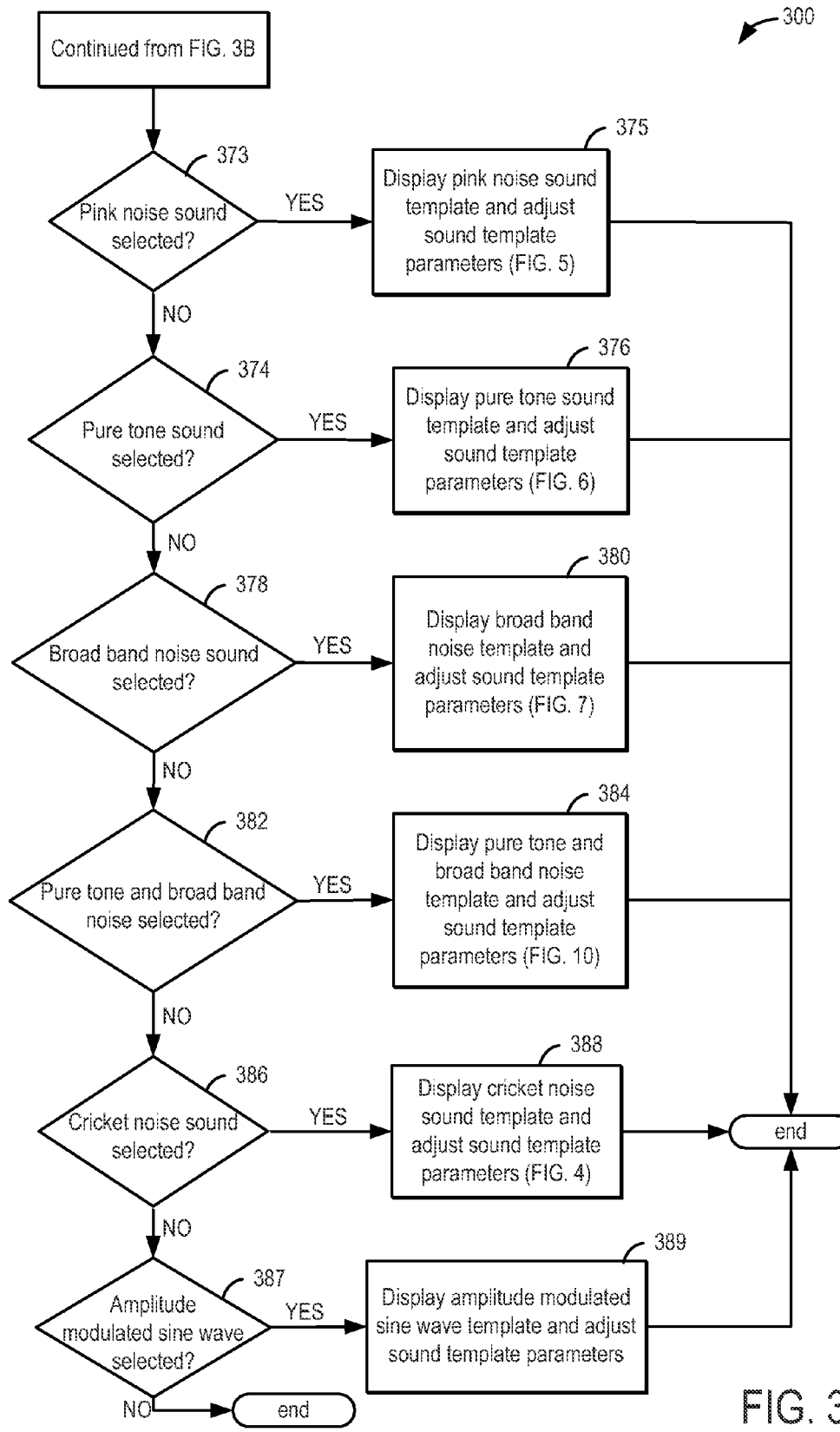

Now referring to FIG. 3A-C, an example method 300 for generating the sound survey, including adjusting tinnitus sound templates is shown. The sound survey may include inputting hearing threshold data determined by an audiogram and selecting tinnitus therapy sound templates in order to create a tinnitus therapy sound. As such, a tinnitus therapy sound template may be selected based on the similarity of the tinnitus therapy sound template (e.g. tinnitus sound type) to the patient's perceived tinnitus. The sound survey is an initial step in generating a tinnitus therapy sound such that the template(s) selected will be adjusted following the conclusion of the sound survey as described further below with regard to FIGS. 4-10.

FIG. 3A shows example tinnitus therapy sound template selections including sound template adjustment parameters. Creating a tinnitus therapy may include presenting each of a white noise, a pink noise, a pure tone, a broad band noise, a combined pure tone and broad band noise, a cricket noise, and an amplitude modulated sine wave tinnitus therapy sound template to a user. In an alternate embodiment, creating a tinnitus therapy may include presenting a different combination of these sound templates to a user. For example, creating a tinnitus therapy may include presenting each of a white noise, a pink noise, a pure tone, a broad band noise, and a cricket noise tinnitus therapy sound template to a user. In yet another example, creating the tinnitus therapy may include presenting each of a white noise, a pure tone, and a combined tone tinnitus therapy sound template to a user. The combined tone may be a combination of at least two of the above listed sound templates. For example, the combined tone may include a combined pure tone and broad band noise tinnitus therapy sound template.

After playing each of the available tinnitus therapy sound templates, the user may select which sound type, or sound template, most resembled their perceived tinnitus. In this way, generating a tinnitus therapy sound may be based on the tinnitus therapy sound template selected by the user. After selecting one or more of the tinnitus therapy sound templates, the selected sound template may be adjusted to more closely resemble the patient's perceived tinnitus. Adjusting the tinnitus therapy sound, or tinnitus therapy sound template, may be based on at least one of a frequency parameter and an intensity parameter selected by the user. As discussed above, a tinnitus therapy sound template may be selected if the tinnitus therapy sound resembles the perceived tinnitus sound of a patient. However, in one example, a patient's perceived tinnitus sound may not resemble any of the tinnitus therapy sound templates. As such, at 358, an unable to match input may be selected. Upon selection of an individual tinnitus therapy sound template, a tinnitus therapy sound template may include adjustment inputs including adjustments for frequency, intensity, timbre, Q factor, vibrato, reverberation, and/or white noise edge enhancement. The pre-determined order of adjustments of the tinnitus therapy sound template(s) selections are described below with regard to FIG. 3A.

FIG. 3A begins at 302, by selecting a white noise sound template. White noise sound template adjustments may include, at 304, adjustments for intensity and adjustments for reverberation, at 306, as described below with regard to FIG. 5. For example, adjusting the tinnitus therapy sound may be first based on the intensity parameter and second based on a reverb input when the tinnitus therapy sound template selected by the user is the white noise tinnitus therapy sound template. If a pink noise template is selected at 303, the pink noise sound template may be adjusted based on intensity at 305 and reverberation at 307. Adjustments to the pink noise sound template may be similar to adjustments to the white noise sound template and is described in further details below with regard to FIG. 5. For example, adjusting the tinnitus therapy sound may be first based on the intensity parameter and second based on a reverb input when the tinnitus therapy sound template selected by the user is the pink noise tinnitus therapy sound template.

In another example, a pure tone sound template, at 308, may be selected. A pure tone sound template may be adjusted based on frequency, at 310, and intensity, at 312. In addition, a pure tone sound template may be further adjusted base on timbre, at 314. In one example, timbre may include an adjustment of an octave and/or harmonics of a tinnitus therapy sound, described further below with regard to FIG. 6. A harmonic adjustment may include an adjustment of a fifth harmonic. Further, a pure tone sound template may be adjusted based on a reverberation, at 316, and a white noise edge enhancement, at 318. In one example, adjusting the tinnitus therapy sound may be first based on the frequency parameter, second based on the intensity parameter, third based on one or more timbre inputs, further based on a reverberation (e.g., reverb) input, and fifth based on an edge enhancement input when the tinnitus therapy sound template selected by the user is the pure tone sound template. In another example, a white noise edge enhancement may be a pre-defined tinnitus therapy sound template. Herein, a white noise edge enhancement sound template may be referred to as a frequency windowed white noise sound template. Additionally, a white noise edge enhancement adjustment may include adjusting the frequency windowed white noise based on an intensity input.

Continuing with FIG. 3A, a broad band noise sound template, at 320, may be selected. A broad band noise sound template may include an adjustment for frequency, Q factor, and intensity, at 322, 324, and 326, respectively. Further adjustments to a broad band noise sound template may include reverberation, at 328, and white noise edge enhancement, at 330 as described further with regard to FIG. 7. For example, adjusting the tinnitus therapy sound may be first based on the frequency parameter, second based on a Q factor input, third based on the intensity parameter, fourth based on a reverb input, and fifth based on an edge enhancement input when the tinnitus therapy sound template selected by the user is the broad band noise tinnitus therapy sound template.

At 332, a combination tinnitus sound template may be selected. A combination tinnitus sound template may include both a pure tone and a broad band noise sound. As such, the combination pure tone and broad band noise sound template may include adjustments for frequency, Q factor, and intensity, at 334, 336, and 338, respectively. A combination pure tone and broad band noise sound template may include further adjustments for timbre, reverberation, and white noise edge enhancement, at 340, 342, and 344, respectively, as described below with regard to FIG. 10. For example, adjusting the tinnitus therapy sound may be first based on the frequency parameter, second based on a Q factor input, third based on the intensity parameter, fourth based on a timbre input, fifth based on a reverb input, and sixth based on an edge enhancement input when the tinnitus therapy sound template selected by the user is the combined pure tone and broad band noise tinnitus therapy sound template.

At 346, a cricket noise sound template may be selected. A cricket noise sound template may include adjustments for frequency, at 348, and intensity, at 350. Further adjustments to a cricket noise template may include a vibrato adjustment, at 352. A vibrato adjustment may include adjustment to the relative intensity of the cricket noise sound template, as further described below with regard to FIG. 4. A cricket noise sound template may also include adjustments for reverberation, at 354, and white noise edge enhancement, at 356. For example, adjusting the tinnitus therapy sound may be first based on the frequency parameter, second based on the intensity parameter, third based on a vibrato input, fourth based on a reverb input, and fifth based on an edge enhancement input then the tinnitus therapy sound template selected by the user is the cricket noise tinnitus therapy sound template.

At 355, an amplitude modulated sine wave sound template may be selected. In one example, the amplitude modulated sine wave template may include a base wave and carrier wave component. Additionally, the amplitude modulated sine wave template may include adjustments for intensity (e.g., amplitude) at 357, or alternatively adjustment to the base wave frequency. In alternate embodiments, additional or alternative adjustments may be made to the amplitude modulated sine wave sound template.

In another embodiment, the tinnitus therapy sound template(s) may include a plurality of tinnitus therapy sounds including but not limited to the tinnitus therapy sounds mentioned above with regard to FIG. 3A. For example, FIG. 3A may include alternative or additional sound templates which may be displayed and played for the user. Specifically, in one example, an additional combination tinnitus sound template may be presented to and possibly selected by the user. In one example, the additional combination tinnitus therapy sound template may include a combined white noise and broad band noise sound template. In another example, the additional combination tinnitus therapy sound template may include a template combining more than two tinnitus therapy sound types.

It should be appreciated that once a user selects a sound template and its properties (such as intensity or frequency), no additional modulation is applied to the selection. Further it should be appreciated that once a user selects a sound level, treatment or therapy where the selected sound is replayed occurs at the selected sound level without lowering.

Referring now to FIG. 3B, method 300 begins at 360 by obtaining audiogram data via an audiogram input and/or patient hearing data. The audiogram input may include hearing threshold data. In one example, the hearing threshold data may be determined at an earlier point in time during a patient audiogram. An individual patient's hearing threshold data may include decibel and frequency data. As such, the frequency, expressed in hertz (Hz), is the "pitch" of a sound where a high pitch sound corresponds to a high frequency sound wave and a low pitch sound corresponds to a low frequency sound wave. In addition, a decibel (dB) is a logarithmic unit that indicates the ratio of a physical quantity relative to an implied reference level such that the physical quantity is a sound pressure level. Therefore, the hearing threshold data is a measure of an individual patient's hearing level or intensity (dB) and frequency (Hz). Additionally, the audiogram input and/or patient hearing data may be received by various methods. In another example, a user interface may prompt a user to perform a hearing test in order to obtain audiogram data, as described below with regard to FIG. 25.

Based on a generated audiogram from the hearing test, a user may input hearing level and frequency data when prompted by the user interface. In yet another example, the audiogram input of patient hearing data may be uploaded to the healthcare professional's device via a wireless network, a portable storage device, or another wired device. In another example, the audiogram or patient hearing data may be input by the user (e.g., medical provider) with the user interface of the healthcare professional's device.

At 362, the method includes determining if the hearing threshold data from the audiogram has been received. Once the audiogram data has been received, at 364, the initial tinnitus therapy sound template settings (e.g. frequency and intensity) may be modified by the hearing threshold data from an individual patient's audiogram. For example, in order for the tinnitus therapy sound template to be in the correct hearing range of an individual patient, specific frequency and intensity ranges may not be included in the tinnitus therapy sound template. Specifically, if an audiogram's hearing threshold data reflects mild hearing loss of a patient (e.g. 30 dB, 3000 Hz), the frequency and intensity range associated with normal hearing will be eliminated from the template default settings (e.g. 0-29 dB; 250-2000 Hz) such that a default setting starts at the hearing level of the patient. In another example, the hearing threshold data from an individual patient's audiogram may be used to determine sensitivity thresholds (e.g. intensity and frequency) of the tinnitus therapy sound. For example, hearing threshold data may include maximum intensity and frequency thresholds for an individual patient such that the tinnitus therapy sound template's intensity and/or frequency may not be greater than a patient's sensitivity threshold. As such, the sensitivity levels will further limit the intensity and frequency range of the tinnitus therapy sound template. As such, the frequency and intensity range of the tinnitus therapy sound template may be based on the hearing level and hearing sensitivity of the patient. Therefore, at 364, the tinnitus therapy sound template(s) default settings are adjusted to reflect the audiogram, hearing threshold data, and hearing sensitivity of the patient.

At 366, a plurality of tinnitus therapy sound templates may be displayed. In one example, the tinnitus therapy sound templates may include tinnitus sounds including cricket noise, white noise, pink noise, pure tone, broad band noise, amplitude modulated sine wave sound, and a combination of pure tone and broad band noise. Specifically, each tinnitus therapy sound template may be pre-determined to include one of the above listed tinnitus sounds having pre-set or default sound characteristics or template settings (e.g., frequency, intensity, etc.). As described above, in other examples more or less than 5 different tinnitus therapy sound templates may be displayed.

At 368, the tinnitus therapy sound template selection process begins by playing pre-defined tinnitus therapy sounds (e.g., sound templates). In one example, the pre-defined tinnitus therapy sounds may be played in a pre-determined order including playing a white noise sound first followed by a pink noise sound, pure tone sound, a broad band sound, a combination pure tone and broad band sound, a cricket noise sound, and an amplitude modulated sine wave sound. In another example, the tinnitus therapy sounds may be played in a different order. Further, the different tinnitus therapy sounds may either be presented/played sequentially (e.g., one after another), or at different times. For example, the sound templates may be grouped into sound categories (e.g., tonal or noise based) and the user may be prompted to first select between two sound templates (e.g., cricket and white noise).

Based on the user's selection, another different pair of sound templates (or tinnitus therapy sounds) may be presented and the user may be prompted to select between the two different sound templates. This process may continue until one or more of the tinnitus therapy sound templates are selected. In this way, the method 300 may narrow in on a patient's tinnitus sound match by determining the combination of sound templates included in the patient's perceived tinnitus sound.

Figure 3D:
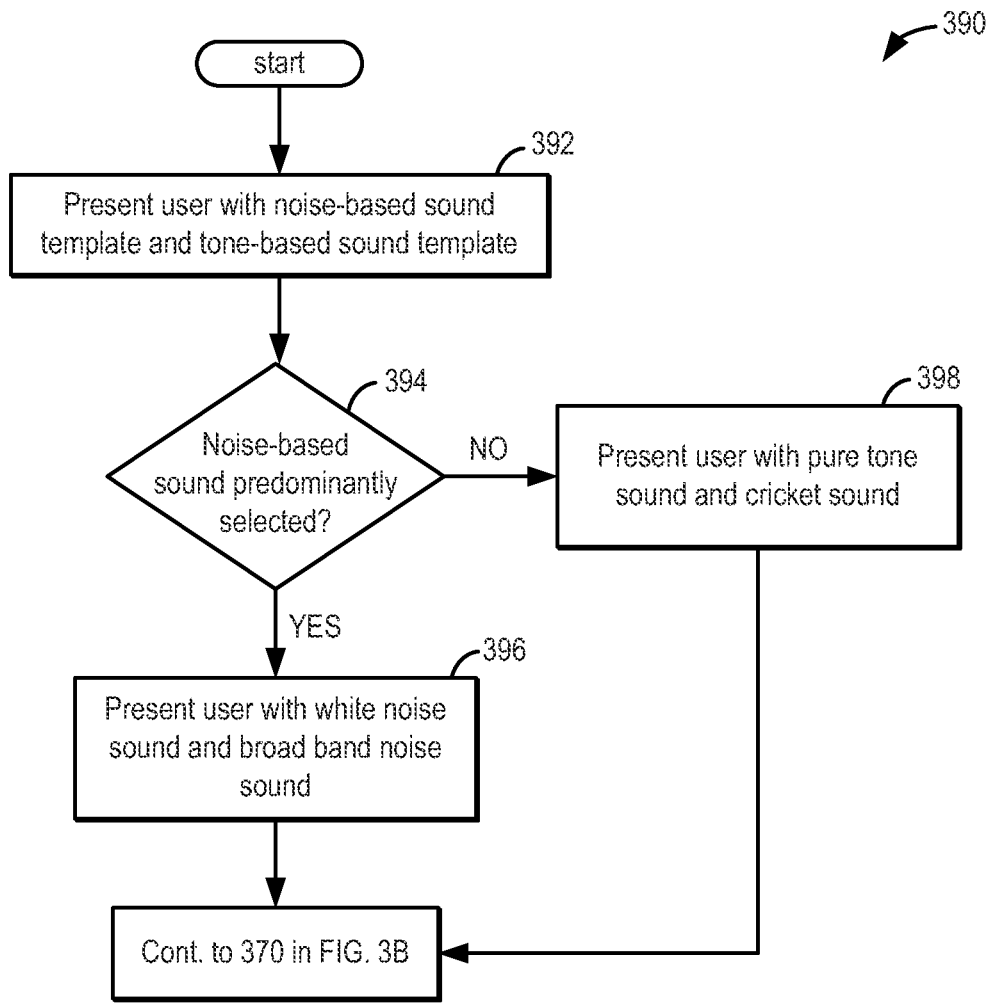

FIG. 3D presents an example method 390 of an order of presenting the different tinnitus therapy sounds (e.g., sound templates) to the user. As such, method 390 may be performed during step 368 in method 300. At 392, the method includes presenting a user, via a user interface of the healthcare professional's device, with a noise-based sound template and a tone-based sound template. The noise-based sound template may be a white noise sound template, a broad band noise sound template, a pink noise sound template, or some combination template of the white noise, broad band noise, and/or pink noise sound templates. The tone-based sound template may be a pure tone sound template, a cricket sound template, or some combined pure tone and cricket sound template.

At 394, the method includes determining if the noise-based sound was predominantly selected. In one example, the noise-based sound may be predominantly selected if an input selection of the noise-based sound is received. In another example, the user interface of the healthcare professional's device may include a sliding bar between the noise-based and tone-based sounds. In this example, the noise-based sound may be predominantly selected if an input (e.g., a sliding bar input) is received indicating the tinnitus sound is more like the noise-based sound than the tone-based sound. If an input of a predominantly noise-based sound is received, the method continues on to 396 where the method includes presenting the user with a white noise sound, a pink noise sound, and/or a broad band noise sound. The method then returns 370 in FIG. 3B. Conversely at 394, if the noise-based sound is not predominantly selected, the method continues on to 398 to present the user with a pure tone sound and a cricket sound. The method then returns to 370 in FIG. 3B. Other methods of presenting the different sound types (e.g., templates) to a user are possible and may include presenting the sound templates in different combinations and/or orders.

Following the presentation of the tinnitus therapy sound template, the user interface of the healthcare professional's device will display a prompt to the user confirming the tinnitus therapy sound template selection. For example, confirming the tinnitus therapy sound template selection may include selecting whether the selected sound template is similar to the patient's perceived tinnitus. At 370, the method 300 includes determining if a white noise sound is selected. In one example, a white noise sound may be selected if the presented white noise sound resembles a patient's perceived tinnitus. At 370, if a white noise sound is selected as a tinnitus sound similar to that of the patient's, the method continues on to 372 to display a white noise sound template, as described below with regard to FIG. 5. In one example, upon selection of a tinnitus therapy sound template, a tinnitus sound, corresponding to the selection, will be presented to the user. Following the presentation of the tinnitus therapy sound template, a user interface will display a prompt to the user confirming the tinnitus therapy sound template selection (e.g. white noise sound template). Once the tinnitus therapy sound template is selected, the user interface will display the tinnitus therapy sound template on the tinnitus therapy sound screen.

Method 300 continues to 373 in FIG. 3C where the method includes determining if a pink noise sound template is selected. If a pink noise sound template is selected as a tinnitus sound similar to that of the patient's, the method continues to 375 to display a pink noise sound template, as described below with regard to FIG. 5. If pink noise is not selected, the method continues on to 374 where the method includes determining if a pure tone sound template is selected. If a pure tone sound template is selected as a tinnitus sound similar to that of the patient's, at 376, the pure tone sound template is displayed in the and further adjustment to the pure tone sound template may be made, as described further below with regard to FIG. 6. If a pure tone sound is not selected, at 378, the method includes determining if a broad band noise sound is selected. If a broad band sound template is selected as a tinnitus sound similar to that of the patient's, at 380, the broad band noise sound template is displayed and further adjustment to the broad band noise sound template may be made, as described further below with regard to FIG. 7.

If a broad band noise sound is not selected, at 382, the method includes determining if a combination of pure tone and broad band noise sound is selected. If a combination of pure tone and broad band noise sound template is selected as a tinnitus sound similar to that of the patient's, at 384, the combination pure tone and broad band noise sound template is displayed and further adjustment to the combination pure tone and broad band noise sound template may be made, as described further below with regard to FIG. 10.

If a combination of pure tone and broad band noise sound is not selected, at 386, the method includes determining if a cricket noise sound is selected. In one example, the user interface of the healthcare professional's device will prompt a user to select a cricket noise sound template. If the cricket noise sound template is selected, at 388, a user interface will display a cricket noise sound template as described further below with regard to FIG. 4.

If the cricket noise sound template is not selected at 386, the method continues to 387 to determine if an amplitude modulated sine wave template is selected. If the amplitude modulated sound template is selected, at 389, a user interface will display the amplitude modulated sine wave template. A user may then adjust an intensity and/or additional sound parameters of the sine modulated sine wave template. After any user inputs or adjustments, the method may include finalizing the tinnitus therapy sound including the amplitude modulated sine wave template.

An individual patient's perceived tinnitus may incorporate a plurality of tinnitus sounds; therefore, the method 300 may be repeated until all required templates have been selected. For example, a patient's perceived tinnitus may have sound characteristics of a combination of tinnitus sounds including white noise and broad band noise, white noise and pure tone, or pure tone and broad band noise, as described further below with regard to FIGS. 8-10. In yet another example, the patient's perceived tinnitus may include sound characteristics of two or more tinnitus sounds including two or more of white noise, pink noise, broad band noise, pure tone, amplitude modulated sine wave, and cricket. Additionally, the tinnitus therapy sound generated based on the selected tinnitus therapy sound templates may contain different proportions of the selected sound templates. For example, a generated tinnitus therapy sound may contain both pure tone and cricket sound components, but the pure tone component may make up a larger amount (e.g., 70%) of the combined tinnitus therapy sound.

Figure 4:
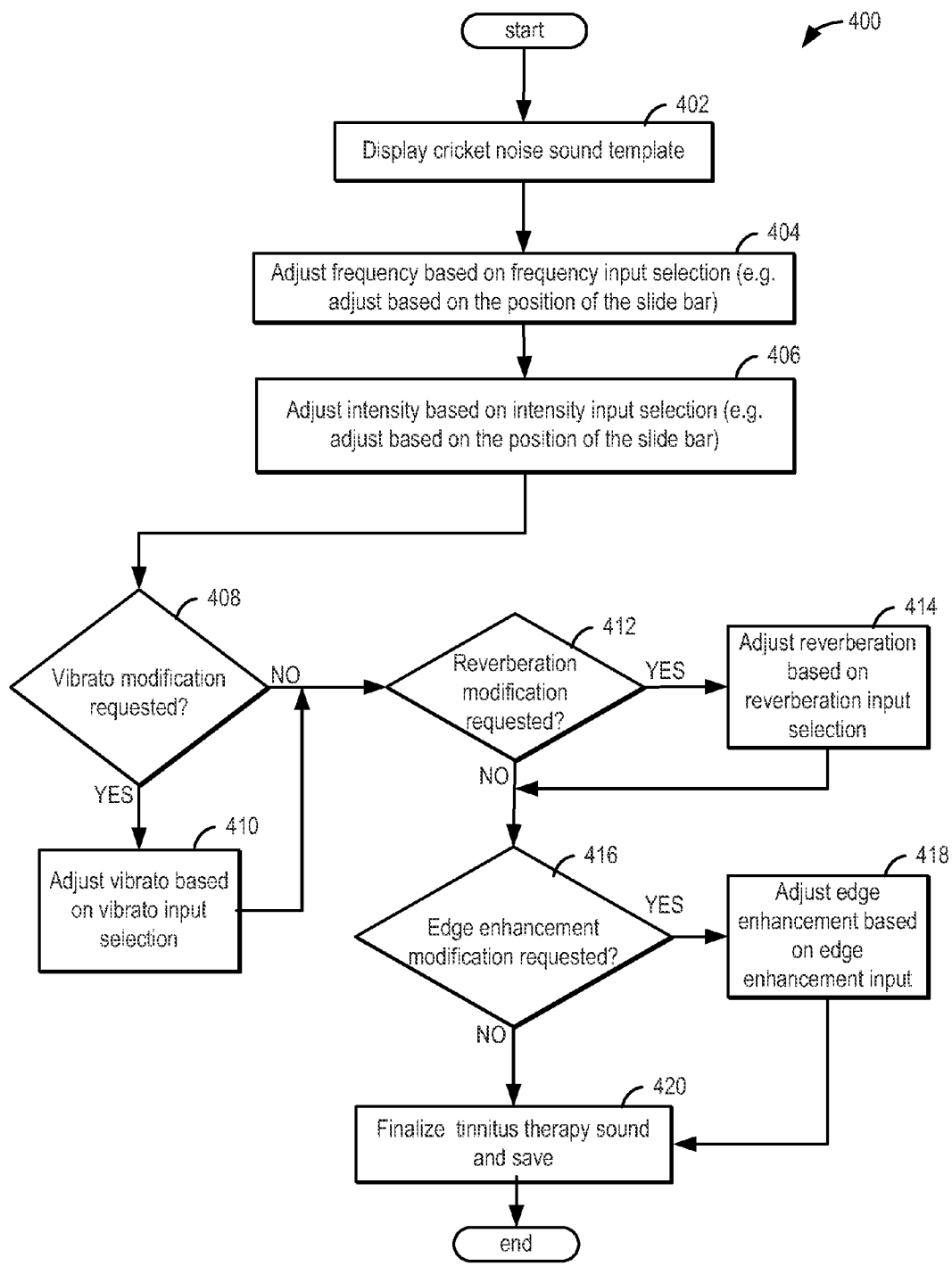
FIG. 4 shows an example method for generating a tinnitus therapy sound for a cricket noise sound template.
Figure 16:
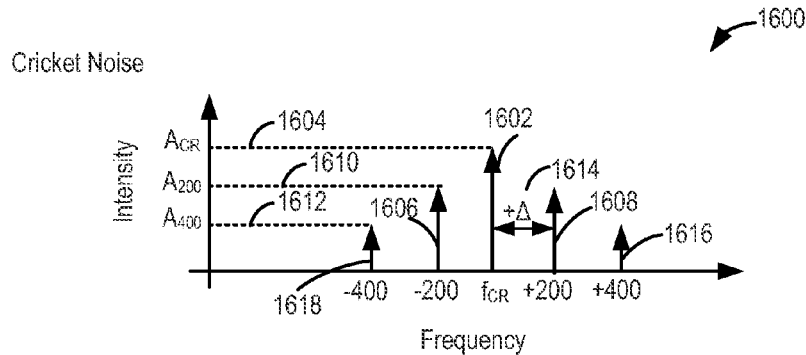
FIG. 16 shows an example graph of a cricket noise sound template.

Referring now to FIG. 4, an example method 400 for generating a cricket noise sound, or tinnitus sound match is shown. The cricket noise sound template display includes adjustments for central frequency and intensity. Further, the cricket noise sound template includes the presence of vibrato that does not occur in the other tinnitus therapy sound templates. In one example, the vibrato adjustment may include adjustment of the relative frequencies based on a relative intensity adjustment of the cricket noise sound. FIG. 16 shows a graph 1600 of an example cricket noise sound template. Specifically, graph 1600 shows intensity, or amplitude, on the y-axis and frequency on the x-axis. The cricket noise sound template includes a cricket noise sound waveform. The cricket noise sound waveform may include a combination of pure tones. As such, the cricket noise template may be referred to herein as a combined tinnitus therapy sound template including more than one type of sound. As shown in FIG. 16, the cricket noise sound waveform includes a central frequency, $f_{CR}$, shown at 1602. The cricket noise waveform also includes one or more relative frequencies shown at 1608, 1616, 1606, and 1618. Each relative frequency is defined relative to the central frequency. For example, the central frequency shown at 1602 and the relative frequency shown at 1608 are separated by a delta frequency, $\Delta$, as shown at 1614. The delta frequency shown in FIG. 16 is a positive relative frequency of 200 Hz. In other examples, the relative frequency may be a frequency larger or smaller than 200 Hz. Further, each of the central frequency and the relative frequencies may have an intensity, or amplitude. For example, the central frequency has an amplitude 1604 which is higher than the amplitude 1610 of the relative frequency shown at 1606 and the amplitude 1612 of the relative frequency shown at 1618. The cricket noise sound template may be pre-defined with a pre-defined central frequency, relative frequency, or frequencies, and amplitudes of each respective frequency. As described further below, during method 400, the central frequency, relative frequency, and intensity of the cricket noise sound template may be adjusted based on user input via the user interface of the healthcare professional's device.

In addition, the adjustment features for the cricket noise sound template are pre-defined and may be further modified in order to reflect the hearing threshold data input from the template selection process, as described above with reference to FIG. 3A. As such, the adjustments may generate a tinnitus therapy sound that resembles an individual patient's perceived tinnitus.

At 402, the method includes displaying the cricket noise sound template display. For example, a user interface may include a tinnitus therapy sound display including a cricket noise sound template display following the tinnitus sound template selection process. Additionally, the cricket noise sound template display may include adjustment input buttons. Adjustments to the cricket noise sound template through the cricket noise sound template display, described further below, may generate a cricket noise sound.

Once the cricket noise sound template display is displayed in the tinnitus sound display, at 404, the frequency adjustment input will be at a pre-defined position based on the audiogram input from a user, as mentioned above with regard to FIG. 3A. In one example, users may further adjust the frequency of the cricket noise sound template through the user interface. For example, the frequency adjustment may include adjustment of a central and relative frequency of the cricket noise sound template. As such, the user interface may include a display for a cricket sound template including adjustment input buttons (e.g. slide bars) for modifying the central and relative frequencies of the tinnitus therapy sound template. At 406, the central frequency of the cricket noise sound template is adjusted based on the position of the central frequency slide bar. The frequency may be further adjusted by a relative frequency input selection. In one example, the relative frequencies may include a central frequency of +200 Hz, −200 Hz, +400 Hz, or −400 Hz with pre-determined intensities. Specifically, a relative frequency of a central frequency of +200 Hz may have larger amplitude than a relative frequency of central frequency of +400 Hz.

Following the frequency adjustments, at 406, the method includes adjusting the intensity of the central frequency of the cricket noise sound template. Further, adjusting the intensity may include adjusting both a right ear and left ear together. In one example, the intensity input may include an adjustable right and left ear intensity input slide bar(s), or other adjustable input button and the input slide bars may be moved simultaneously. In another example, the adjustment of the intensity may be performed for each ear. As such, a right ear and left ear input slide bar(s) may be adjusted separately. Further, the intensity may be adjusted based on decibel increments. In one example, the intensity adjustment may be adjusted in 0.5 dB increments. In another example, the intensity adjustment may be adjusted in 1.0 dB increments. In yet another example, the intensity adjustment may be adjusted in 2.0 dB increments. In another example, the intensity adjustment may be adjusted in some increment between 0.5 and 2.0 dB.

Following the intensity adjustment, at 408, the method includes determining if a vibrato modification is requested. If vibrato modification is request, the method continues on to 410 to adjust the vibrato based on an input selection. In one example, the vibrato modification may include adjusting the intensity of the relative frequencies. Adjustments to the vibrato of the cricket noise sound may be based on user input through the user interface. In one example, adjusting the central frequency of a cricket noise may automatically change the intensity of the relative frequencies. Specifically, the relative frequency adjustment may be proportional to the central frequency adjustment. In another example, the relative intensity input may include an adjustable right and left ear intensity input slide bar(s), or other adjustable input button and the input slide bars may be moved simultaneously. In another example, the adjustment of the relative intensity may be performed for each ear. As such, a right ear and left ear input slide bar(s) may be adjusted separately.

Figures 22A, 22B:
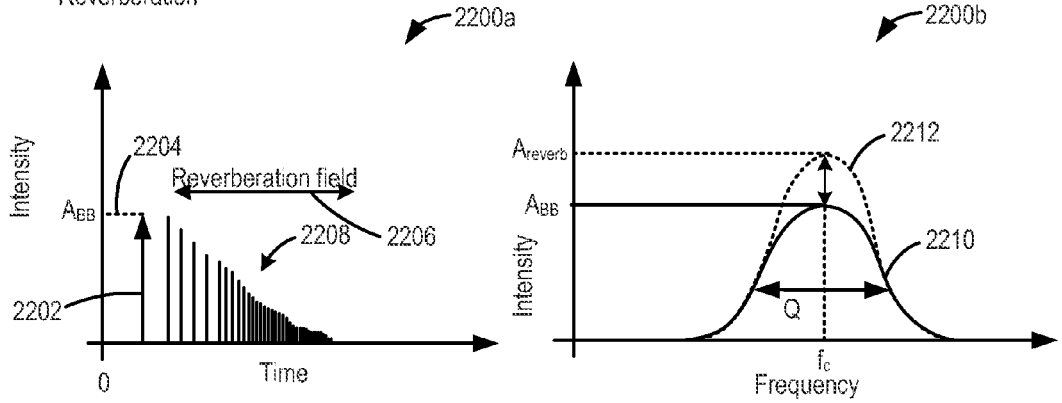
FIG. 22 A-B shows example graphs of a broad band noise template with reverberation.
Figure 23:
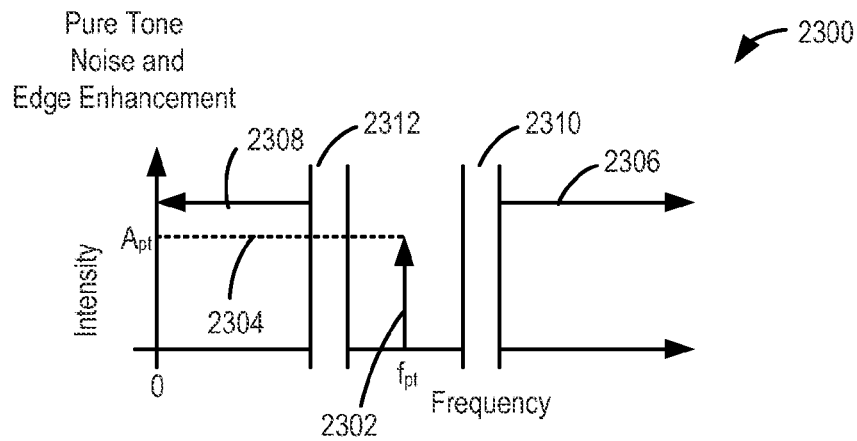
FIG. 23 shows an example graph of a pure tone template with a white noise edge enhancement.
Figure 24:
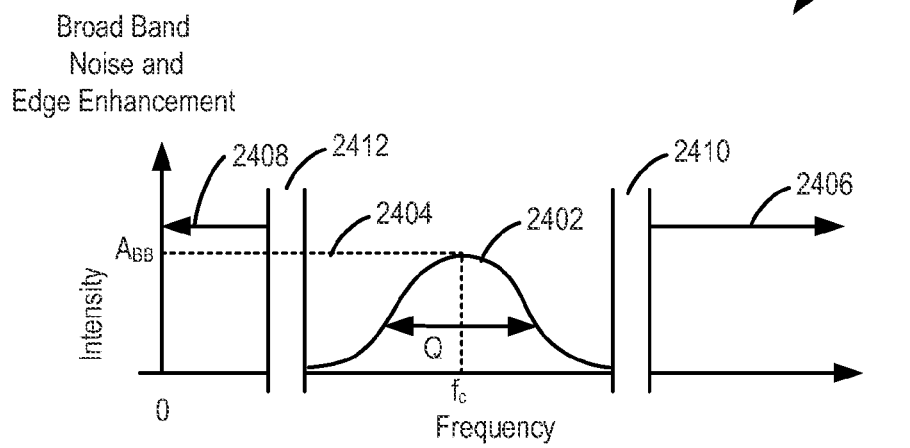
FIG. 24 shows an example graph of a broad band noise template with a white noise edge enhancement.

Following the intensity adjustments, at 412, the method includes determining if a reverberation modification is requested. Reverberation may be a rapid, modified repetition of a sound blended with the original tinnitus therapy sound, thereby creating an echo effect. If a reverberation modification is requested, at 414, reverberation of the cricket noise may be adjusted based on an input selection. An example of reverberation added to a different tinnitus therapy sound template is shown at FIG. 22A, described further below. Following reverberation modification, the method at 416 includes determining if a white noise edge enhancement modification is requested. A white noise edge enhancement may include a frequency windowed white noise adjustment. In one example, white noise, at a pre-determined frequency, may be added to the cricket noise sound. In another example, the pre-determined frequency of the white noise edge enhancement may be based on a patient's audiogram. An example of white noise edge enhancement added to a different tinnitus therapy sound template is shown at FIGS. 23-24, described further below. Following reverberation and/or white noise edge enhancement modification, at 420, the tinnitus therapy sound may be finalized and saved to the healthcare professional's device. In one example, finalization of the sound or tinnitus sound match may include setting therapy parameters, with reference to FIG. 1D, and may also include presenting the adjusted sound to the user. For example, a user interface may include an input button for a user to select in order to play the finalized tinnitus therapy sound or tinnitus sound match. In another example, an intermittence of the cricket noise sound template may also be adjusted by the user during method 400.

Figure 5:
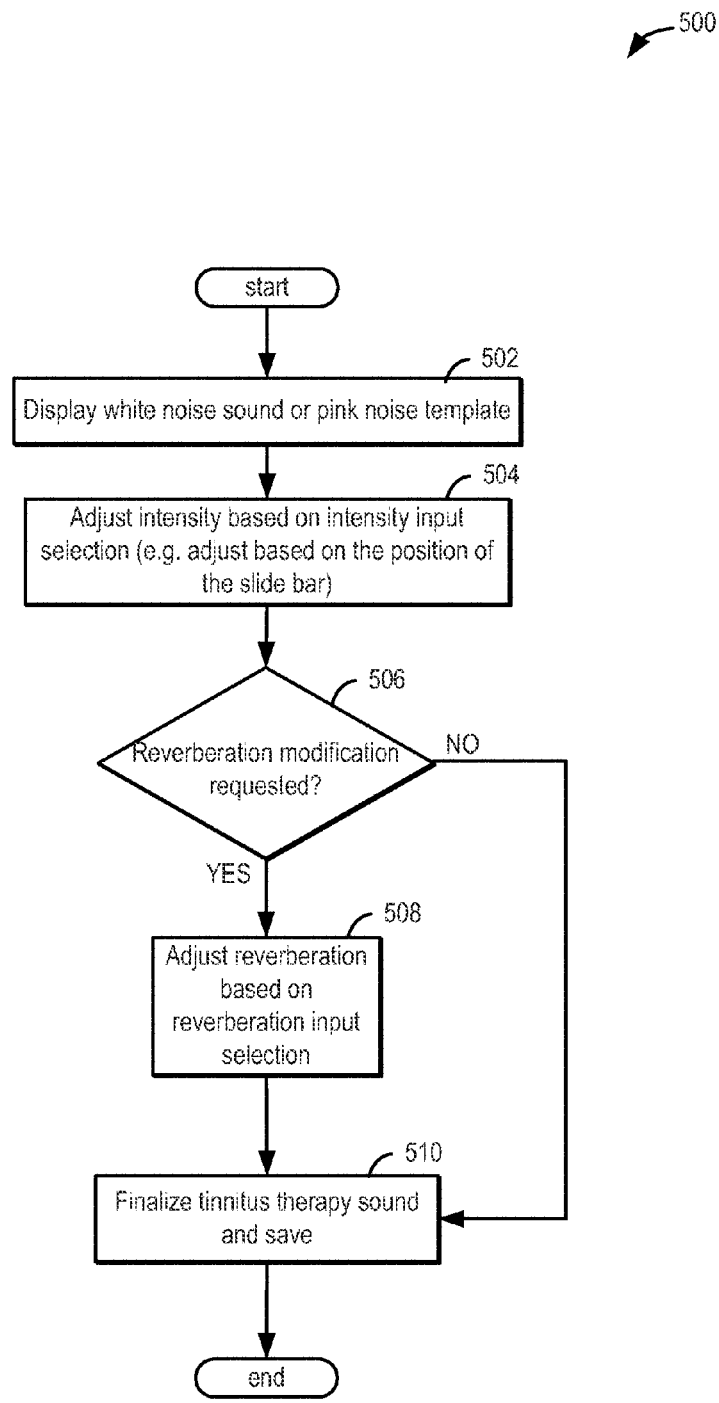
FIG. 5 shows an example method for generating a tinnitus therapy sound for a white noise or a pink noise sound template.
Figure 13:
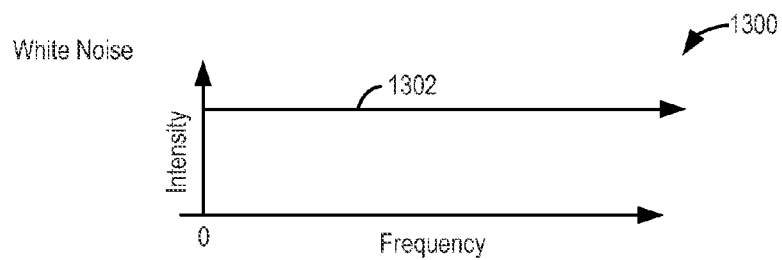
FIG. 13 shows an example graph of a white noise sound template.

Referring now to FIG. 5, an example method 500 for generating a white noise or a pink noise sound is shown. A white noise sound is a random signal with a flat power spectral density. FIG. 13 shows a graph 1300 of an example white noise sound template. Specifically, graph 1300 shows intensity, or amplitude, on the y-axis and frequency on the x-axis. The white noise sound template includes a white noise sound waveform. The white noise sound waveform includes a signal including all frequencies at a specified intensity, as shown at 1302. The white noise sound template may be pre-defined with a pre-defined intensity. As described further below, during method 500, the intensity of the white noise sound template may be adjusted based on user input via the user interface of the healthcare professional's device.

Figure 26:
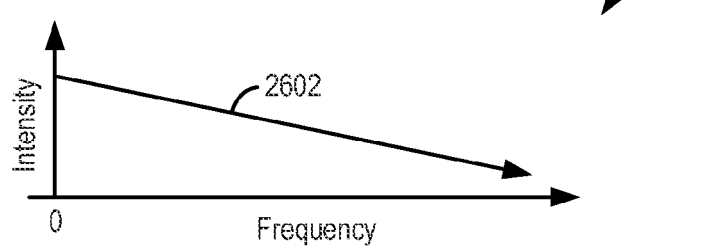
FIG. 26 shows an example graph of a pink noise sound template.

A pink noise sound is a signal with a power spectral density that is inversely proportional to the frequency of the signal. In pink noise, each octave carries an equal intensity level. FIG. 26 shows a graph 2600 of an example pink noise sound template. Specifically, graph 2600 shows intensity on the y-axis and frequency on the x-axis. The pink noise sound template includes a pink noise sound waveform. The pink noise sound waveform includes a signal decreasing in intensity by approximately 3 dB per octave over a range of all frequencies, as shown at 2602. The pink noise sound template may be pre-defined with a pre-defined intensity at a frequency of zero. As described further below, during method 500, the zero-frequency intensity (e.g., y-intercept) of the pink noise sound template may be adjusted based on user input via the user interface of the healthcare professional's device.

Since a white noise and pink noise sounds include a plurality of frequencies, the white noise sound template and the pink noise sound template may not include adjustments for frequency. In some examples, the white noise or pink noise sound templates may include adjustments for intensity and reverberation. The adjustment inputs may be pre-set, or initially adjusted, in order to reflect the hearing threshold data input during the template selection process, as described above with reference to FIG. 3A. As described below, further adjustments made to the white noise sound template or pink noise sound template may generate a sound or tinnitus sound match that resembles an individual patient's perceived tinnitus.

At 502, the method includes displaying a white noise or a pink noise sound template display. For example, a user interface may include a tinnitus therapy sound display with a white noise or pink noise sound template display following the tinnitus therapy sound template selection process, as described above with regard to FIG. 3A-B. In one example, the white noise or pink noise sound template display may include adjustment inputs for intensity and reverberation. A position or change in position of these adjustment inputs may adjust the white noise or pink noise sound template, thereby adjusting the respective white noise or pink noise sound heard by the patient or user. Adjustments to the white noise or pink noise sound template may result in the generation of a white noise or pink noise sound or tinnitus sound match, respectively, that resembles an individual patient's perceived tinnitus. The intensity adjustment inputs of the displayed sound template display may be at a pre-determined position. The pre-determined position may be specified in the template selection process, as described above with reference to FIG. 3A. In one example, once the sound template is displayed, a user (e.g., patient) may be presented with a white noise or pink noise sound based on the default settings, with reference to FIG. 1C. Since white noise and pink noise include substantially all frequencies (e.g. substantially all frequencies within a hearing range, such as the hearing range of a human ear), only the intensity of the white noise or pink noise sound may be adjusted in one example. Adjustment of the sound template, at 504, may begin once the selected sound template display is displayed.

At 504, the method may include adjusting the intensity of the sound template based on an intensity input selection. Further, adjusting the intensity may include adjusting both a right ear and left ear intensity. The intensity input may include an adjustable right and left ear intensity input slide bar(s) or other adjustable input button. In one example, the input slide bars may be moved together. For example, moving one of the right or left ear slide bar may automatically move the other of the right or left ear slide bar. In another example, the adjustment of the relative intensity may be performed for each ear. As such, a right ear and left ear input slide bar(s) may be adjusted separately. Further, the intensity may be adjusted based on decibel increments. In one example, the intensity adjustment may be adjusted by 0.5 dB increments. In another example, the intensity adjustment may be adjusted by 1.0 dB increments. In yet another example, the intensity adjustment may be adjusted by 2.0 dB increments.

At 506, the method includes determining if a reverberation modification is requested. If a reverberation modification is requested, at 508, reverberation of the sound template is adjusted based on an input selection. The reverberation modification may include increasing/decreasing a reverberation time, or sound decay rate, in one example. While not repeated for each of the different templates, similar reverb adjustments may be used as described herein.

Following the reverberation adjustments, at 510, the white noise or pink noise sound or tinnitus sound match may be finalized and saved to the healthcare professional's device. In one example, finalization of the sound or match may include setting therapy parameters, with reference to FIG. 1D, and may also include presenting the adjusted sound to the user. In some embodiments, an intermittence of the sound template may also be adjusted by the user during method 500.

Figure 6:
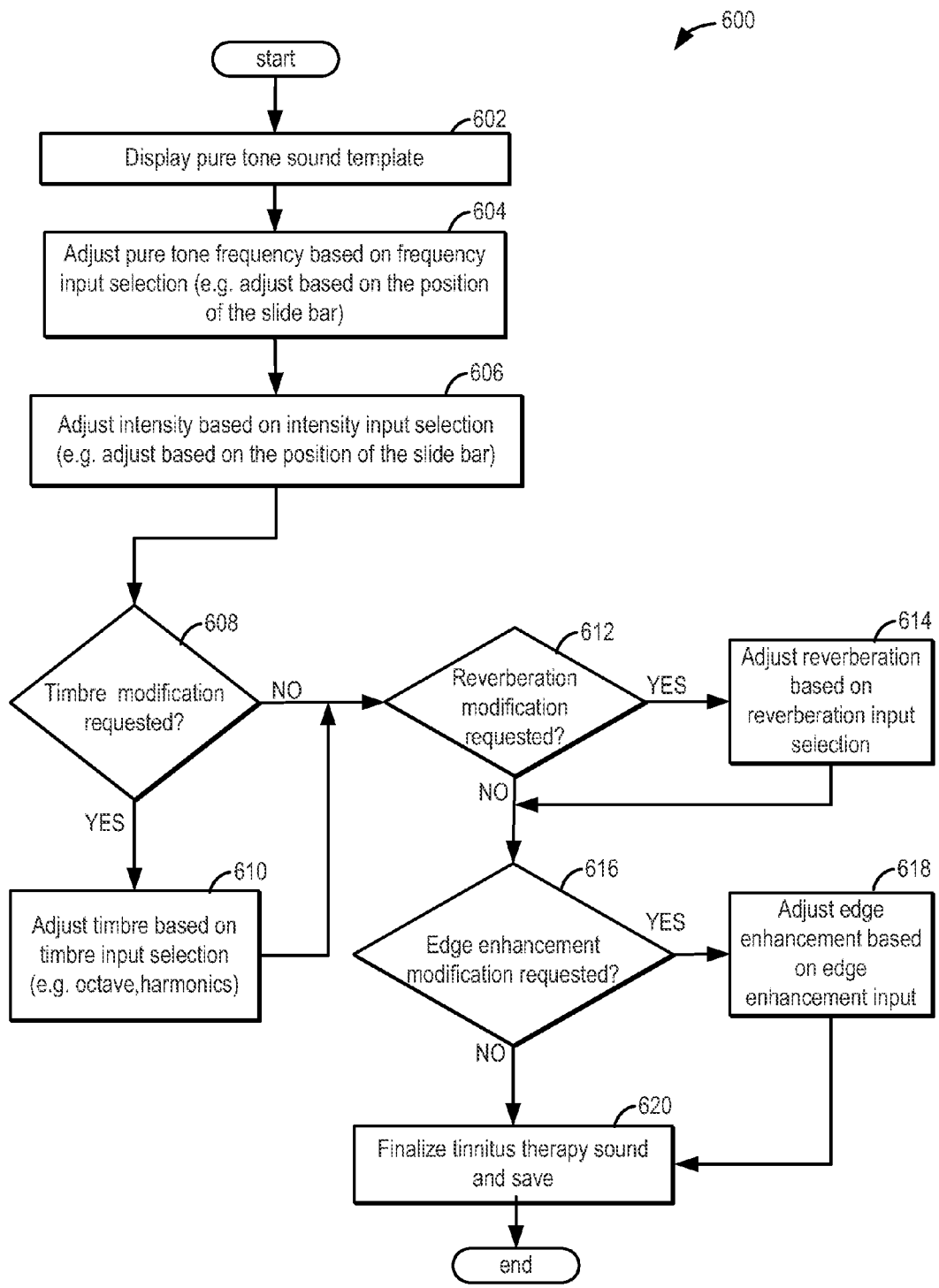
FIG. 6 shows an example method for generating a tinnitus therapy sound for a pure tone sound template.
Figure 14:
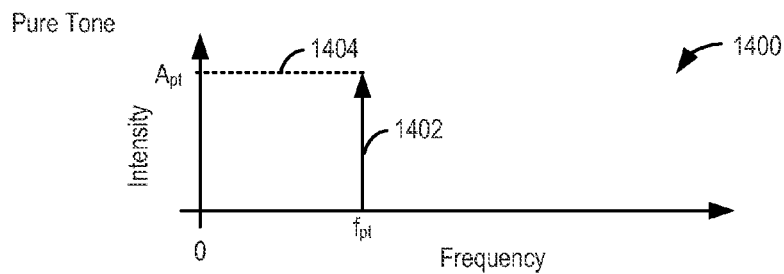
FIG. 14 shows an example graph of a pure tone sound template.

FIG. 6 shows an example method 600 for generating a pure tone sound or tinnitus sound match. Specifically, a pure tone is a steady sound of a single frequency produced by simple harmonic vibrations and without overtones. FIG. 14 shows a graph 1400 of an example pure tone sound template. Specifically, graph 1400 shows intensity, or amplitude, on the y-axis and frequency on the x-axis. The pure tone sound template includes a pure tone sound waveform. The pure tone sound waveform includes a single or central frequency, $f_{pt}$, shown at 1402. The central frequency has a specific intensity, or amplitude, as shown at 1404. The pure tone sound template may be pre-defined with a pre-defined central frequency and intensity. As described further below, during method 600, the central frequency and intensity of the pure tone sound template may be adjusted based on user input via the user interface of the healthcare professional's device.

Figure 17:
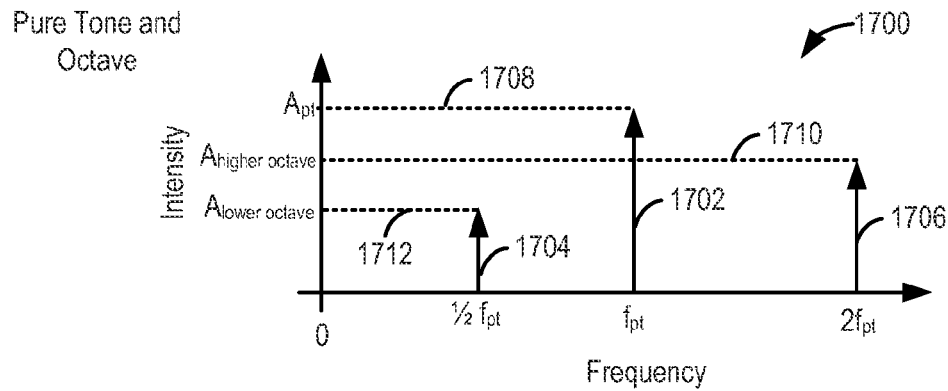
FIG. 17 shows an example graph of a pure tone sound template with octave adjustment.

The pure tone sound template display includes adjustments for frequency and intensity, as well as optional timbre, reverberation, and/or white noise edge enhancement modification. Timbre may include octave and/or harmonic adjustments. In one example, a harmonic adjustment may include a fifth harmonic adjustment. Further, an octave is the interval between two frequencies, where one frequency is the double of the other, for example, 125 Hz and 250 Hz. Specifically, any two sounds whose frequencies make a 2:1 ratio are separated by an octave. As such, the introduction of timbre into a sound template may change the harmonics of the tinnitus therapy sound match. FIG. 17 shows a graph 1700 of an example pure tone sound template with octave adjustment. Specifically, graph 1700 shows the central frequency at 1702 with an added higher octave shown at 1706 and a lower octave shown at 1704. In one example, either a higher or lower octave may be added to and adjusted in the pure tone sound template. In another example, one or more of a higher octave and a lower octave may be added to and adjusted in the pure tone sound template. Each of the central frequency, the higher octave, and the lower octave has a specific amplitude shown at 1708, 1710, and 1712, respectively. As described further below, during method 600, one or more octaves may be added to and adjusted in the pure tone sound template based on user input via the user interface of the healthcare professional's device.

The adjustment features of the pure tone sound template may also be pre-set to reflect the hearing threshold data input from the template selection process, as described above with reference to FIG. 3A. As such, further adjustments made to the pure tone sound template may generate a sound match that more closely resembles an individual patient's perceived tinnitus. For example, a user interface may include an input button for a user to select in order to play the finalized tinnitus therapy sound to the patient.

At 602, the method includes displaying the pure tone sound template display. For example, a user interface may include a tinnitus therapy sound display including a pure tone sound template display following the tinnitus therapy sound template selection process. In one example, the pure tone sound template display may include adjustment input buttons. When a pure tone template is selected, the pure tone template's frequency will be at a pre-defined, or pre-set, position based on the audiogram input from a user, as mentioned above with regard to FIG. 3A. In one example, the user interface may include a display for a pure tone sound template display including adjustment input buttons (e.g. slide bars) for modifying the frequency, intensity, timbre, reverberation, and white noise edge enhancement of the tinnitus sound template.

At 604, the method includes adjusting the frequency of the pure tone sound template based on the position of the frequency adjustment slide bar, or other frequency adjustment input. Following the frequency adjustment, at 606, the intensity may be adjusted including adjusting both a right ear and left ear. The intensity input may include an adjustable right and left ear intensity input slide bar(s) or other adjustable input button. In one example, the input slide bars may be moved simultaneously. In another example, the adjustment of the intensity may be performed for each ear. As such, a right ear and left ear input slide bar(s) may be adjusted separately. Further, the intensity may be adjusted based on decibel increments. In one example, the intensity adjustment may be adjusted by 0.5 dB increments. In another example, the intensity adjustment may be adjusted by 1.0 dB increments. In yet another example, the intensity adjustment may be adjusted by 2.0 dB increments.

At 608, the method includes determining if a timbre modification of the pure tone sound template is requested. A timbre modification may include adjustment of an octave and/or harmonics of the pure tone sound template. If the timbre modification is not requested, at 612, the method includes determining if a reverberation modification is requested. Returning to 616, a timbre modification may be requested based on, for example, if the user's perceived tinnitus sound is either "brighter" or "darker" than the pure tone sound match. If a request for timbre modification is received, at 618, the octave and/or harmonic input may be adjusted based on user input via the user interface. In one example, if a higher octave is selected, the sound match may have a "brighter" sound; however, if a lower octave is selected, the sound match may have a "darker" sound. In another example, a fifth harmonic input may be selected and adjusted.

At 612, the method includes determining if a reverberation modification is requested. If a reverberation modification is requested, at 614, reverberation of the pure tone sound template may be adjusted based on an input selection. Further, at 616, the method includes determining if a white noise edge enhancement modification is requested. A white noise edge enhancement may include a frequency windowed white noise adjustment. In one example, white noise, at a pre-determined frequency, may be added to the pure tone sound. In another example, the pre-determined frequency of the white noise edge enhancement may be based on a patient's audiogram. FIG. 23 shows a graph 2300 of an example pure tone sound template with white noise edge enhancement. Specifically, graph 2300 shows the frequency of a pure tone, at 2302, with a pure tone amplitude, at 2304. Graph 2300 further shows an added frequency windowed white noise (e.g. white noise edge enhancement) at 2306 and 2308, respectively. In one example, frequency windowed white noise may be added at a pre-determined frequency such that the white noise intensity may be greater than the pure tone intensity. In another example, the addition of the white noise edge enhancement may include sections where no tinnitus sounds are present, such as areas before and after the pure tone sound, as shown at 2310 and 2312, respectively. As described above, during method 600, white noise edge enhancement may be added to and adjusted in the pure tone sound template based on user input via the user interface of the healthcare professional's device.

The method at 612 includes finalizing the pure tone sound saving the sound to the healthcare professional's device. Finalization of the tinnitus sound match may include setting therapy parameters, with reference to FIG. 1D, as well as presenting the adjusted pure tone sound match to a user. For example, a user interface may include an input button for a user to select in order to play the finalized tinnitus sound match. In some embodiments, an intermittence of the pure tone sound template may also be adjusted by the user during method 600.

Figure 7:
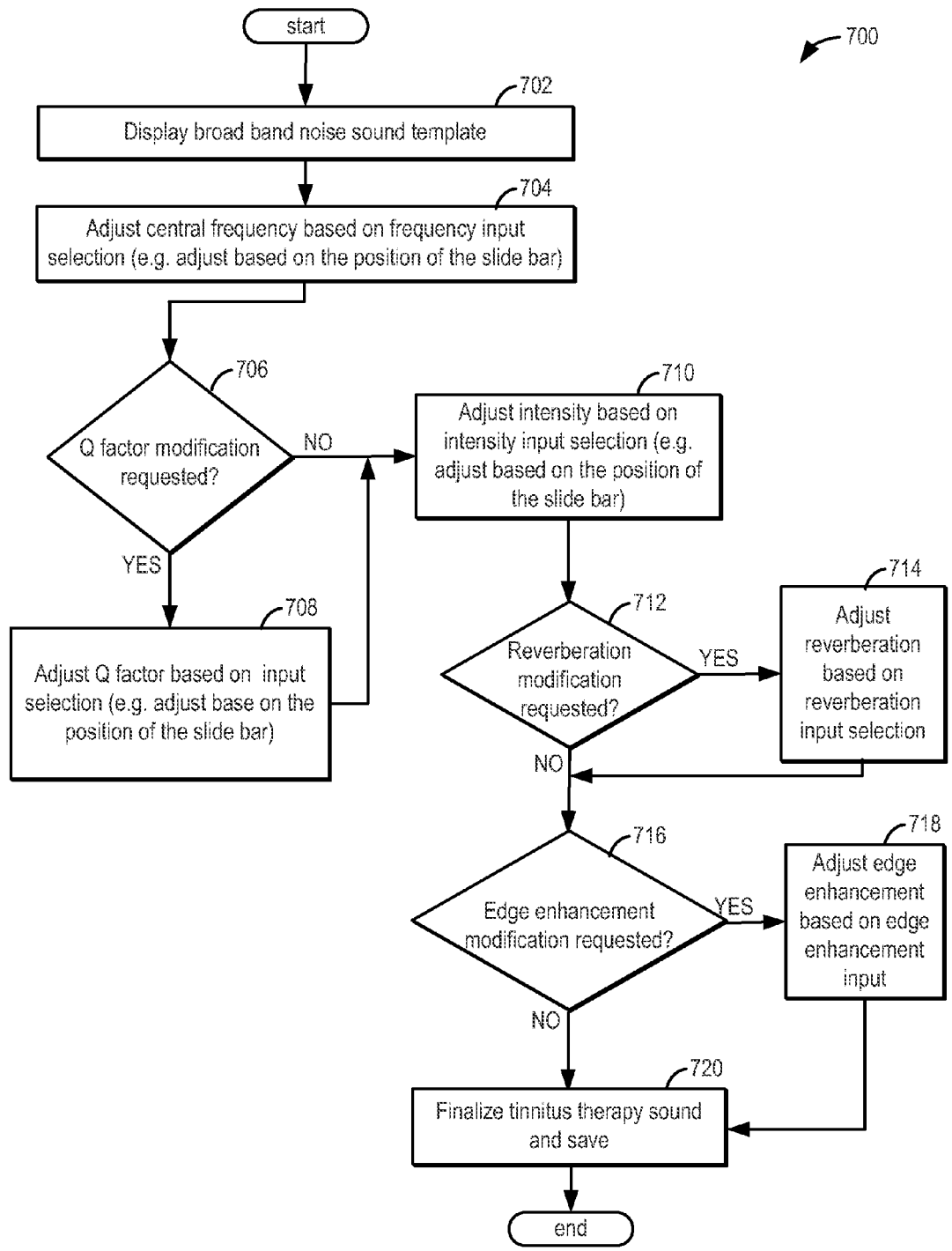
FIG. 7 shows an example method for generating a tinnitus therapy sound for a broad band noise sound template.

Referring now to FIG. 7, an example method 700 for adjusting a broad band noise sound template is shown. Broad band noise is a filtered white noise with a central frequency and a certain range of surrounding frequencies according to a quality factor (Q factor). The broad band noise sound template may include adjustments for frequency and intensity, as well as additional modifications for Q factor, reverberation, and white noise edge enhancement.

Figure 15:
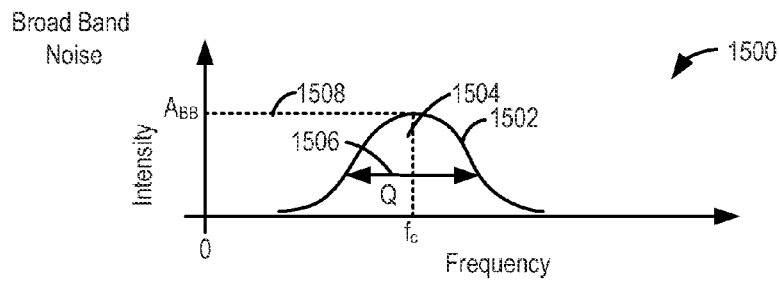
FIG. 15 shows an example graph of a broad band noise sound template.

FIG. 15 shows a graph 1500 of an example broad band noise sound template. Specifically, graph 1500 shows intensity, or amplitude, on the y-axis and frequency on the x-axis. The broad band noise sound template includes a broad band noise sound waveform 1502. The broad band noise sound waveform 1502 includes a central frequency, $f_c$, shown at 1504. The central frequency has a specific intensity, or amplitude, as shown at 1508. The broad band noise sound waveform 1502 also includes a Q factor, shown at 1506, which defines a bandwidth, or range of frequencies, of the broad band noise sound waveform 1502.

The pure tone sound template may be pre-defined with a pre-defined central frequency and intensity. As described further below, during method 600, the central frequency and intensity of the broad band noise sound template may be adjusted based on user input via the user interface of the healthcare professional's device.

In addition, the adjustment features may be pre-defined (e.g., set within specific ranges or values) in the broad band noise template based on the hearing threshold data input from the tinnitus therapy sound template selection process, as described above with reference to FIG. 3A. As such, the adjustments may generate a tinnitus therapy sound or tinnitus sound match that more closely resembles an individual patient's perceived tinnitus.

At 702, the method includes displaying a broad band noise template display. For example, a user interface may include a tinnitus sound match display with a broad band noise sound template display following the tinnitus therapy sound template selection process. In one example, the broad band noise sound template display may include adjustment input buttons. In one example, a user interface may include a display for the broad band noise template display including adjustment input buttons (e.g. slide bars) for modifying frequency, intensity, Q factor, reverberation, and white noise edge enhancement.

At 704, the central frequency of the broad band noise template may be adjusted based on an input selection. In one example, the input selection may be determined based on the position of a slide bar, or other adjustable frequency input button. For example, adjusting the central frequency of the broad band noise template may include increasing or decreasing a pre-set, or default, central frequency based on the position of the frequency adjustment slide bar.

At 706, the method includes determining if a Q factor modification is requested. The Q factor determines the width of a range of frequencies known as bandwidth. In one example, the adjustment of a Q factor changes the bandwidth of a sound signal such that the Q factor may increase or decrease the range of frequencies relative to the central frequency. If a Q factor modification is requested, at 708, a Q factor may be adjusted based on an input selection from a user (e.g. based on the position of a slide bar). For example, if the Q factor is adjusted (e.g., decreased) such that the sound has a lower Q factor, the frequency of the sound may have a wider bandwidth than a higher Q factor. Conversely, if the Q factor is adjusted (e.g., increased) such that the broad band noise sound has a higher Q factor, the frequency of the sound may have a narrower bandwidth than a lower Q factor.

At 710, the method includes adjusting the intensity including adjusting both a right ear and left ear. The intensity input may include an adjustable right and left ear intensity input slide bar(s) or other adjustable input button. In one example, the input slide bars may be moved simultaneously. In another example, the adjustment of the intensity may be performed for each ear. As such, a right ear and left ear input slide bar(s) may be adjusted separately. Further, the intensity may be adjusted based on decibel increments. In one example, the intensity adjustment may be adjusted by 0.5 dB increments. In another example, the intensity adjustment may be adjusted by 1.0 dB increments. In yet another example, the intensity adjustment may be adjusted by 2.0 dB increments.

At 712, the method includes determining if a reverberation modification is requested. If a reverberation modification is requested, at 714, reverberation of the broad band noise sound template may be adjusted based on an input selection. FIG. 22A-B shows graphs of example broad band noise sound templates including reverberation. Specifically, FIG. 22A shows a graph 2200a including intensity, or amplitude, on the y-axis and time on the x-axis. The broad band noise sound, 2202, has a specific amplitude, 2204. Reverberation may include a reverberation field, 2206, including a reverberation time and reverberation reflections 2208. Reverberation time may be the time it takes the reverberation reflection amplitudes to decrease until the sound can no longer be heard. Therefore, reverberation may occur after a broad band noise, 2202, stops but the reflections continue over time. In another example, the length of the reverberation time may correspond to the frequency of the broad band noise. FIG. 22B shows a graph 2200b including a broad band noise sound template including a broad band noise sound waveform 2210. The broad band noise sound waveform 2210 includes a central frequency, $f_c$, and the central frequency has a specific intensity, or amplitude. The broad band noise sound waveform 2210 may include reverberation field, shown at 2212. Specifically, a broad band sound waveform 2210 may include a reverberation field 2212, such that the frequency of the broad band sound waveform does not change but the broad band noise amplitude may be adjusted due to the reverberation field, shown at 2212.

Further, at 716, the method includes determining if a white noise edge enhancement modification is requested. A white noise edge enhancement may include a frequency windowed white noise adjustment. In one example, white noise, at a pre-determined frequency, may be added to the broad band noise sound. In another example, the pre-determined frequency of the white noise edge enhancement may be based on a patient's audiogram. FIG. 24 shows a graph 2400 of an example broad band noise sound template with white noise edge enhancement. Specifically, graph 2400 shows the broad band noise central frequency, at 2402, with an amplitude, at 2404. Graph 2400 further shows an added frequency windowed white noise (e.g. white noise edge enhancement) at 2406 and 2408, respectively. In one example, frequency windowed white noise may be added at a pre-determined frequency such that the white noise intensity may be greater than the broad band noise intensity. In another example, the addition of the white noise edge enhancement may include sections where no tinnitus sounds are present, such as areas before and after the broad band noise sound, as shown at 2410 and 2412, respectively. As described above, during method 700, white noise edge enhancement may be added to and adjusted in the broad band noise sound template.

At 720, the broad band noise sound or tinnitus sound match may be finalized and saved to the healthcare professional's device. As such, finalization of the sound match may include setting specific therapy parameters, with reference to FIG. 1D. For example, a user interface may include an input button for a user to select in order to play the finalized sound match. In some embodiments, an intermittence of the broad band noise sound template may also be adjusted by the user during method 700.

FIGS. 8-10 show example methods for adjusting a combination tinnitus therapy sound including a white noise sound template combined with a broad band noise sound template (FIG. 8), a white noise sound template combined with a pure tone sound template (FIG. 9), and a pure tone sound template combined with a broad band noise sound template (FIG. 10). The combination tinnitus sound templates may be based on user selection from the sound survey, as described above with regard to FIGS. 3A-B. A combined tinnitus sound may be generated based on adjustments made to each individual sound, or template, of the combination sound or tinnitus sound match.

In one example, generating a combined tinnitus therapy sound may include receiving a selection of a first tinnitus therapy sound template and then receiving a selection of a second tinnitus therapy sound template. The first tinnitus therapy sound template and the second tinnitus therapy sound template may be selected individually or simultaneously. Further, sound parameters of the first and second tinnitus therapy sound templates may be individually adjusted before being combined into the combined tinnitus therapy sound Alternatively, the first and second tinnitus therapy sound templates may be combined into the combined tinnitus sound match and then sound parameters of the combined tinnitus sound match may be adjusted. In another example, generating a combined tinnitus therapy sound may include receiving a selection of three different tinnitus therapy sound templates. The combination tinnitus therapy sound may include two or more of a cricket noise sound template, a white noise sound template, a pure tone sound template, and/or a broadband noise sound template.

Referring now to FIG. 8, an example method 800 for generating a combination tinnitus therapy sound including a white noise sound template combined with a broad band noise sound template is shown. At 802, the method includes displaying white noise and broad band noise sound template displays. For example, a user interface may include a tinnitus therapy sound display with a white noise sound template display and a broad band noise sound template display following the tinnitus sound template selection process. Adjustment of the combined tinnitus therapy sound may begin with the individual adjustment of the broad band noise template, as described above with regard to FIG. 7. At 804, the central frequency of the broad band noise template is adjusted based on the frequency input selection. The adjustment of the broad band noise sound template continues, at 806, where it is determined if a Q factor modification is requested. If Q factor modification is requested, at 808, the Q factor may be adjusted based on an input selection, such as a position of a Q factor slide bar, or other Q factor adjustable input.

At 810, the method includes adjusting the intensity of the combined white noise and broad band noise sound template. Adjusting the intensity may include adjusting both a right ear and left ear. The intensity input may include an adjustable right and left ear intensity input slide bar(s) or other adjustable input button. In one example, the input slide bars may be moved simultaneously. In another example, the adjustment of the intensity may be performed for each ear. As such, a right ear and left ear input slide bar(s) may be adjusted separately. Further, the intensity may be adjusted based on decibel increments. In one example, the intensity adjustment may be adjusted by 0.5 dB increments. In another example, the intensity adjustment may be adjusted by 1.0 dB increments. In yet another example, the intensity adjustment may be adjusted by 2.0 dB increments.

At 812, the method includes determining if a reverberation modification is requested. If a reverberation modification is requested, at 814, reverberation of the combined sound template may be adjusted based on an input selection. Further, at 816, the method includes determining if a white noise edge enhancement modification is requested. A white noise edge enhancement may include a frequency windowed white noise adjustment. In one example, white noise, at a pre-determined frequency, may be added to the broad band noise sound. At 820, the combined white noise and broad band noise sound or match may be finalized and saved to the healthcare professional's device. As such, finalization of the tinnitus sound match may include setting specific therapy parameters, with reference to FIG. 1D. For example, a user interface may include an input button for a user to select in order to play the finalized tinnitus sound match. In some embodiments, an intermittence of the combined white noise and broad band noise sound templates may also be adjusted by the user during method 800.

Referring now to FIG. 9, an example method for generating a combination tinnitus therapy sound including a white noise sound template combined with a pure tone sound template is shown. At 902, the method includes displaying white noise and pure tone sound template displays. Adjustment of the tinnitus therapy sound templates begin by adjusting the frequency of the pure tone sound template at 904, as described above with regard to FIG. 6. Following adjustment of the pure tone sound template frequency, at 9106, the method includes adjusting the intensity of the combined white noise and pure tone sound template. Adjusting the intensity may include adjusting both a right ear and left ear. The intensity input may include an adjustable right and left ear intensity input slide bar(s) or other adjustable input button. In one example, the input slide bars may be moved simultaneously. In another example, the adjustment of the intensity may be performed for each ear. As such, a right ear and left ear input slide bar(s) may be adjusted separately. Further, the intensity may be adjusted based on decibel increments. In one example, the intensity adjustment may be adjusted by 0.5 dB increments. In another example, the intensity adjustment may be adjusted by 1.0 dB increments. In yet another example, the intensity adjustment may be adjusted by 2.0 dB increments.

At 908, the method includes determining if a timbre modification is requested. If the timbre modification is not requested, at 912, the method includes determining if a reverberation modification is requested. However, if at 908 a timbre modification is requested, the timbre of the combined tinnitus sound match may be adjusted at 910. The timbre modification may include adjustment of an octave and/or harmonic input, as described above with regard to FIG. 6. At 912, the method includes determining if a reverberation modification is requested. If a reverberation modification is requested, at 914, reverberation of the combined sound template is adjusted based on an input selection. Further, at 916, the method includes determining if a white noise edge enhancement modification is requested. A white noise edge enhancement may include a frequency windowed white noise adjustment. In one example, white noise, at a pre-determined frequency, may be added to combined sound. At 920, the combined white noise and pure tone tinnitus sound match may be finalized and saved to the healthcare professional's device. As such, finalization of the tinnitus sound match may include setting specific therapy parameters, with reference to FIG. 1D. For example, a user interface may include an input button for a user to select in order to play the finalized tinnitus sound match. In some embodiments, an intermittence of the combined white noise and pure tone sound templates may also be adjusted by the user during method 900.

Referring now to FIG. 10, an example method 1000 for generating a combination tinnitus sound match including a broad band noise sound template with a pure tone sound template is shown. At 1002, the method includes displaying pure tone and broad band noise sound template displays. At 1004, the method includes adjusting the frequency of the combined pure tone and broad band noise sound template, as described above with regard to FIGS. 6 and 7. In one example, the broad band noise sound template central frequency may be adjusted first based on an input selection and a pure tone sound template frequency may be adjusted second based on an input selection. In another example, the broad band noise and pure tone sound frequencies may be adjusted simultaneously.

At 1006, the method includes determining if a Q factor modification is requested. If Q factor modification is requested, at 1008, the Q factor of the tinnitus sound match may be adjusted based on an input selection such as a position of a Q factor slide bar, as described above with regard to FIG. 7.

At 1010, the method includes determining if modification of the intensity is requested. For the combined pure tone and broad band noise sound, adjusting the intensity may include adjusting both a right ear and left ear. The intensity input may include an adjustable right and left ear intensity input slide bar(s) or other adjustable input button. In one example, the input slide bars may be moved simultaneously. In another example, the adjustment of the intensity may be performed for each ear. As such, a right ear and left ear input slide bar(s) may be adjusted separately. Further, the intensity may be adjusted based on decibel increments. In one example, the intensity adjustment may be adjusted by 0.5 dB increments. In another example, the intensity adjustment may be adjusted by 1.0 dB increments. In yet another example, the intensity adjustment may be adjusted by 2.0 dB increments.

At 1012, the method includes determining if a timbre modification is requested. If the timbre modification is not requested, at 1016, the method includes determining if a reverberation modification is requested. However, at 1012, if a timbre modification is requested, the timbre of the combined tinnitus sound match may be adjusted at 1014. The timbre modification may include adjustment of an octave and/or harmonic, as described above with regard to FIG. 6. Following a timbre adjustment, at 1016, the method includes determining if a reverberation modification is requested. If a reverberation modification is requested, at 1018, reverberation of the combined sound template may be adjusted based on an input selection. Further, at 1020, the method includes determining if a white noise edge enhancement modification is requested. A white noise edge enhancement may include a frequency windowed white noise adjustment. In one example, white noise, at a pre-determined frequency, may be added to combined sound. At 1020, if a white noise edge enhancement is not requested, the method includes finalizing a tinnitus therapy sound and saving the tinnitus therapy sound to a healthcare professional's device, at 1024. As such, finalization of the tinnitus sound match may include setting specific therapy parameters, with reference to FIG. 1D. For example, a user interface may include an input button for a user to select in order to play the finalized tinnitus sound match. In some embodiments, an intermittence of the combined pure tone and broad band noise sound templates may also be adjusted by the user during method 1000.

Figure 18:
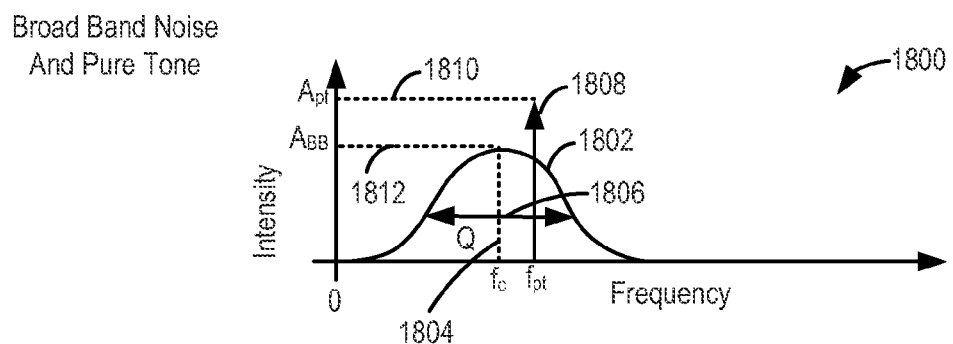
FIG. 18 shows an example graph of a combined broad band noise and pure tone sound template.

FIG. 18 shows a graph 1800 of an example combined broad band noise and pure tone sound template, or tinnitus sound match. Specifically, graph 1800 shows intensity, or amplitude, on the y-axis and frequency on the x-axis. The combined broad band noise and pure tone sound template includes a broad band noise sound waveform 1802 and a pure tone sound waveform 1808. The broad band noise sound waveform 1802 includes a central frequency, $f_c$, as shown at 1804, with a specific intensity, or amplitude, as shown at 1812. The broad band noise sound waveform 1802 also includes a Q factor, shown at 1806, which defines a bandwidth, or range of frequencies, of the broad band noise sound waveform 1802. The pure tone sound waveform 1808 includes a single or central frequency, $f_{pt}$, with a specific intensity, or amplitude, as shown at 1810.

Figure 19:
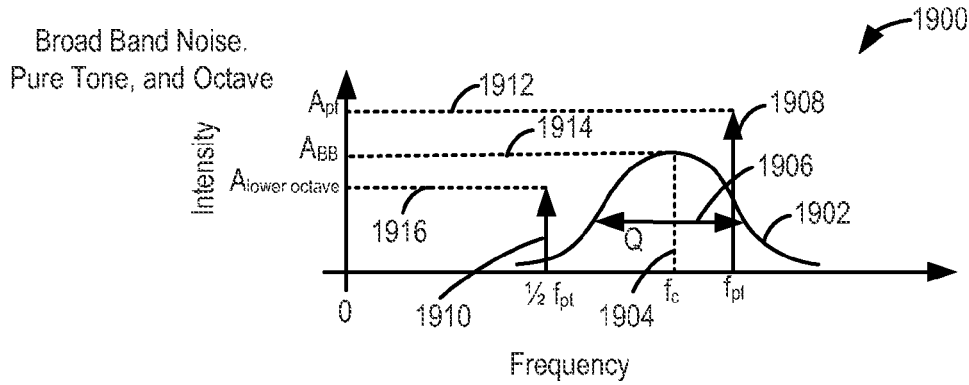
FIG. 19 shows an example graph of a combined broad band noise and pure tone sound template with octave adjustment.

As described above, the combined broad band noise and pure tone sound template, or tinnitus therapy sound, may also include an octave. FIG. 19 shows a graph 1900 of an example combined broad band noise and pure tone sound template, or tinnitus sound match. Specifically, graph 1900 shows intensity, or amplitude, on the y-axis and frequency on the x-axis. The combined broad band noise and pure tone sound template includes a broad band noise sound waveform 1902 and a pure tone sound waveform 1908. The broad band noise sound waveform 1902 includes a central frequency, $f_c$, as shown at 1904, with a specific intensity, or amplitude, as shown at 1914. The broad band noise sound waveform 1902 also includes a Q factor, shown at 1906, which defines a bandwidth, or range of frequencies, of the broad band noise sound waveform 1902. The pure tone sound waveform 1908 includes a single, or central frequency, $f_{pt}$, with a specific intensity, or amplitude, as shown at 1912. A lower octave is also shown at 1910 with a lower octave intensity, as shown at 1916. In alternate examples, the combined broad band noise and pure tone sound template, or tinnitus sound match, may include additional octaves or an octave at a different intensity level.

Figure 20:
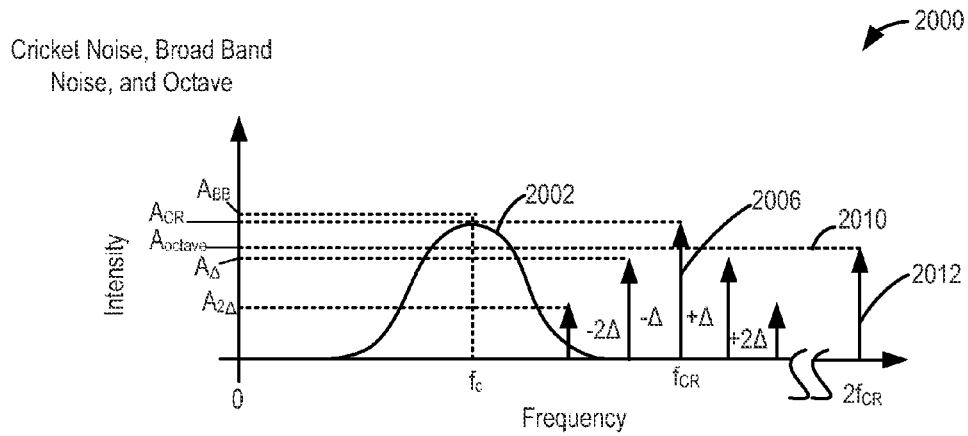
FIG. 20 shows an example graph of a combined cricket noise and broad band noise template with an octave.
Figure 21:
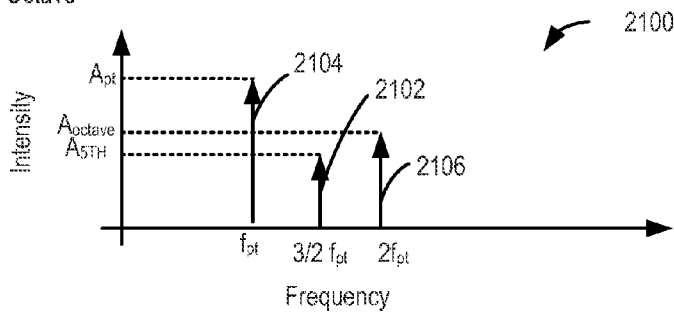
FIG. 21 shows an example graph of a combined pure tone template with a harmonic and an octave.

In other examples, additional combined tinnitus therapy sounds or tinnitus sound matches may be generated to resemble patient's perceived tinnitus. For example, different sound template combinations than those described above at FIGS. 8-10 may be used in generating a tinnitus therapy sound match. In one example, as shown at graph 2000 in FIG. 20, a combined sound template, or tinnitus sound match, may include a cricket noise waveform 2006, a broad band noise waveform 2002, and an octave 2012. In another example, as shown at graph 2100 in FIG. 21, a combined sound template, or tinnitus sound match, may include a pure tone waveform 2104 with a $5^{th}$ harmonic 2102 and an octave 2106. In another example, the combined tinnitus sound match may include a different harmonic with a different intensity and/or an octave with a different intensity than shown in FIG. 21. Other combinations of the different tinnitus sound templates, or types, different that those discussed above may also be used to generate a tinnitus therapy sound for a tinnitus patient.

As described above, a method for generating a tinnitus adjusted sound comprises, receiving a selection of a first tinnitus therapy sound template and a second tinnitus therapy sound template from a series of tinnitus therapy sound templates. Further, the method may include adjusting the first tinnitus therapy sound template and the second tinnitus therapy sound template based on inputs. Additionally, the method may include generating a combined tinnitus therapy sound based on the adjusted first tinnitus therapy sound template and the adjusted second tinnitus therapy sound template. For example, adjusting the first tinnitus therapy sound template and the second tinnitus therapy sound template includes individually adjusting the first tinnitus therapy sound template and the second tinnitus therapy sound template. In one example, the first tinnitus therapy sound template includes white noise and adjusting the first tinnitus therapy sound template includes first adjusting the white noise based on an intensity input and then adjusting the white noise based on a reverb input.

In another example, the first tinnitus therapy sound template includes pure tone. Adjusting the first tinnitus therapy includes firstly adjusting the pure tone based on a frequency input, secondly adjusting the pure tone based on an intensity input, and then adjusting the pure tone based on a reverb input. Further adjusting of the pure tone sound template may include adjusting the pure tone based on a timbre input including adjusting one or more of an octave input and a harmonic input. A harmonic input includes a fifth harmonic.

In another example, the first tinnitus therapy sound template includes broad band noise. Adjusting the broad band noise sound template includes first adjusting the broad band noise based on a frequency input, then adjusting based on a Q factor input, and further adjusting based on an intensity input and a reverb input.

In another example, the first tinnitus therapy sound template includes a pure tone and the second tinnitus therapy sound template includes broad band noise. Adjusting the pure tone sound template includes first adjusting a frequency and intensity input. Further adjusting includes a timbre input including one or more of an octave and harmonic input. The second tinnitus therapy sound template includes first adjusting the broad band noise based on a frequency and Q factor input. Further adjusting includes an intensity input and then a reverb input. Modifying the combined tinnitus therapy sound includes a white noise edge enhancement having an intensity level based on an edge enhancement intensity input.

In another example, the first tinnitus therapy sound template includes cricket noise. Adjusting the cricket noise includes adjusting first based on a frequency input and then on an intensity input. Further adjusting the cricket noise based on a vibrato input and then a reverb input.

In yet another example, the second tinnitus therapy sound template includes a frequency windowed white noise. Adjusting the frequency windowed white noised may be based on an intensity input.

FIG. 11 shows an example method 1100 for recording and tracking patient data. Once a tinnitus therapy sound match (e.g., tinnitus therapy sound) is generated and uploaded onto a patient's device, a patient may be instructed to use the patient's device over a set duration of time. In one example, a patient's device may include data and/or instructions that are executable to play the generated tinnitus therapy sound repeatedly without breaks. In addition, the patient's device may record all performed actions to the device during usage. In one example, the patient's device may also track intensity adjustments to the generated tinnitus therapy sound over time. In this way, a physician may review and track the recorded data, thereby determining the progress of the tinnitus therapy. In addition, the accumulation of an individual patient's tracked data may generate a medical record including a patient audiogram, the tinnitus therapy sound, and a patient adjusted tinnitus therapy sound.

At 1102, the method includes determining if a therapy session has started. In one example, a therapy session may not begin until a start button input is selected on the patient's device (e.g. start therapy input button 40 shown in FIG. 1A). Once the therapy session has started, at 1104, therapy data from the patient's device may be recorded for the duration of the therapy session. In one example, recorded data may include a patient's information, date of the therapy session, time of day the therapy session, and/or volume usage (e.g. changes in intensity). In another example, the recorded volume usage may include changes in intensity to both right and left ear inputs. As such, a user may change the intensity of the tinnitus therapy sound match at the start of the therapy session as well as during the therapy session. In another example, the patient's device may be continuously playing the tinnitus therapy sound without breaks and tracking intensity changes to the continuously played tinnitus therapy sound over time.

At 1106, the method includes determining if the therapy session has ended. For example, in order for a therapy session to end, a finish button input may be selected. Alternatively, the therapy session may end after a therapy duration has passed. If the session has not ended, recording of the therapy data may be continued. Once a finish input has been selected, at 1108, the recorded therapy data may be saved and stored on the patient's device, at 1110. Following the conclusion of a tinnitus therapy session, for example, a plurality of tinnitus therapy sessions may be played on a patient's device. Therefore, an accumulation of recorded data may be saved and stored on a patient's device. At 1112, the recorded therapy data may be uploaded. In one example, the patient's device may receive a signal from a healthcare professional's device (e.g. tablet, desktop computer, etc.) to upload the recorded therapy data. As such, uploading the recorded data may occur wirelessly. In another example, the uploaded data may include date of the therapy session, time of day the therapy session was played, and changes in intensity (e.g. volume usage). In yet another example, therapy data may also include metadata from the patient's device. Further, at 1114, the patient's identification information is uploaded to a healthcare professional's device. In one example, a plurality of recorded data may be uploaded to a healthcare professional's device. As such, a patient medical record (e.g., report) may be generated. In one example, generating a patient medical record may include a patient audiogram, the combined tinnitus therapy sound, and a patient adjusted tinnitus therapy sound.

Further, the uploaded recorded data may be stored and saved on a healthcare professional's device, thereby allowing a physician to track the recorded data over multiple therapy sessions. As such, tracking changes to the therapy session over a duration of time may determine patient progress to the tinnitus therapy. In one example, tracking changes of a patient's device may include remotely tracking intensity changes to the combined tinnitus therapy sound. In another example, tracking changes of a patient's device may include remotely transferring tracked changes to a secured data network. In another example, the tracked therapy data may be used to make changes to the generated tinnitus therapy sound match. In an additional example, tracking changes made to the generated tinnitus therapy sound match over a duration of time may further determine patient progress to the tinnitus therapy.

In an alternate embodiment, the methods presented above at FIGS. 2-11 and below at FIG. 12 for generating a tinnitus therapy sound or tinnitus sound match may also be used to generate a sound match for therapy of other neurological disorders. For example, the generated tinnitus therapy sound may be at least partially used for treating neurological disorders such as chronic pain, epilepsy, Parkinson's disease, and recovery from stroke. In this embodiment, sound templates may be adjusted based on patient data, the patient data being specific to the neurological disorder. In some examples, different combinations of the above described sound templates may be used to generate a therapy sound match for one of the neurological disorders.

Now referring to FIG. 12, an example method 1200 for generating a sound map is shown. A tinnitus sound template selection process may include a visual representation of the patient's tinnitus, with reference to FIGS. 3A-C. In one example, a sound map may be a grid-based representation of sound that may be representative of a patient's perceived tinnitus. As such, a visual representation, such as the sound map, may initially be based on an individual patient's hearing threshold data from an audiogram. In addition, the sound map may change from the initial visual representation based on the template selection and adjustment process of the tinnitus therapy, thereby generating an adjusted sound map.

At 1202, the method includes determining if an audiogram input has been received. For example, audiogram data may include hearing threshold data including a hearing level and frequency. Once an audiogram input has been received, at 1204 a sound map may be generated based on hearing threshold data. At 1206, a plurality of sound templates may be displayed. Sound templates may include cricket noise, white noise, pink noise, amplitude modulated sine wave sound, pure tone, and/or broad band noise, with reference to FIG. 3A. At 1208, the method includes determining if a sound template is selected. If a sound template is selected, at 1210, the sound map may be adjusted based on the sound template selection. In one example, if a cricket noise is not selected, the sound map changes, visually reflecting the subtraction of the cricket noise sound characteristics. Following the template selection process, at 1212, the method includes determining if an adjusted tinnitus therapy sound is finalized. At 1214, the method includes adjusting the sound map based on the adjusted tinnitus therapy sound match. In one example, the sound map may be adjusted following additional adjustment to the tinnitus therapy sound match. As such, the sound map may be tracked over a duration of time, thereby allowing a physician to track a patient's progress to a tinnitus therapy.

Now referring to FIG. 25, an example method 2500 for generating an audiogram is shown including performing a hearing test. A hearing test may be performed during a sound survey including the tinnitus therapy sound template selection process, as described above with reference to FIG. 3B-C. Further, the hearing test data may be used to generate an audiogram. A patient's audiogram may be used to set the pre-defined frequency and intensity parameters of the tinnitus therapy sound template(s).

At 2502, the method includes displaying a hearing test for a user. In one example, a hearing test may include a hearing level and intensity table. The hearing level and intensity table may include a plurality of inputs including hearing level or intensity inputs and frequency inputs. In another example, the hearing level and intensity table may include a range of frequencies and intensities. At 2504, the method includes determining if a hearing level and frequency input selection has been received. If an input selection has not been received, the method continues to display the hearing test. However, if a frequency and intensity input has been received, at 2506, the method includes playing a pre-determined sound based on an input selection. In one example, if a user selects a frequency input and an intensity input, a corresponding sound may be presented to the user. In another example, a user interface may prompt a user to confirm if the sound played is within a user's hearing range. The method, at 2508, includes adjusting the hearing test based on user frequency and intensity input selection. In one example, a hearing level and intensity table may be adjusted to include a range of frequencies and intensities based on the user selection. For example, frequencies and intensities that are not in the range of the user's hearing levels might not be available for selection by the user.

At 2510, the method includes determining if the adjustment of the hearing data is complete. If the adjustment is not complete, the method continues, at 2508, until the adjustment to the hearing data is completed. The method, at 2512, includes generating and displaying an audiogram based on the adjusted hearing data. In one example, based on the user selected inputs, an audiogram might be displayed. An audiogram may include the hearing level and frequency of a patient. In another example, the generated audiogram may be used in the tinnitus therapy sound template selection. Further, the audiogram data may be used to set the pre-defined frequency and intensity levels of the tinnitus therapy sound template, as described above with reference to FIGS. 3B-C.

In this way, a method for generating a tinnitus therapy comprises, presenting each of a white noise, a pure tone, a broad band noise, a combined pure tone and broad band noise, and a cricket noise tinnitus therapy sound template to a user. Further, adjusting the tinnitus therapy sound may be based on at least one of a frequency, intensity, Q factor, timbre, vibrato, reverberation, and white noise edge enhancement parameters. Once a tinnitus therapy is generated, the sound therapy, including the adjusted tinnitus therapy sound, may be transferred from the healthcare professional's device to the patient's device. The patient's device may then present the tinnitus therapy to the patient for a set duration of time. As such, a tinnitus generated therapy, including a tinnitus sound that closely resembles the patient's perceived tinnitus, may be more effective in the treatment of tinnitus.

As another embodiment, a method for creating a tinnitus therapy comprises receiving hearing threshold data from an individual patient audiogram, generating a tinnitus therapy sound based on a pre-defined tinnitus therapy sound template and the hearing threshold data, and modifying the tinnitus therapy sound based on at least one of a frequency input and an intensity input. In some examples, generating the tinnitus therapy sound includes modifying the pre-defined tinnitus therapy sound template based on the hearing threshold data, the pre-defined tinnitus therapy sound template based on a sound type input selected by a patient. In one example, the pre-defined tinnitus therapy sound template includes a white noise sound and modifying the tinnitus therapy sound is based on the intensity input. In another example, the pre-defined tinnitus therapy sound template includes a pure tone sound and modifying the tinnitus therapy sound is further based on timbre, the timbre including one or more of an octave input and a harmonic input. In yet another example, the pre-defined tinnitus therapy sound template includes a broad band noise sound and modifying the tinnitus therapy sound is further based on a Q factor input. In still another example, the pre-defined tinnitus therapy sound template includes a pure tone sound combined with a broad band noise sound and modifying the tinnitus therapy sound is further based on a Q factor input and one or more timbre inputs, the one or more timbre inputs including an octave input and a harmonic input. In another example, the pre-defined tinnitus therapy sound template includes a cricket noise sound and modifying the tinnitus therapy sound is further based on a vibrato input. The method may further comprise modifying the tinnitus therapy sound based on a reverberation input and then finalizing the tinnitus therapy sound. In some examples, the method further comprises further modifying the tinnitus therapy sound to include an edge enhancement having an intensity level based on an intensity input when the pre-defined tinnitus therapy sound template includes one of a pure tone sound, a broad band noise sound, a combined pure tone and broad band noise sound, or a cricket noise sound. Generating the tinnitus therapy sound includes combining a first adjusted tinnitus therapy sound template and a second adjusted tinnitus therapy sound template into a combined sound.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third,"

etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for generating a tinnitus adjusted sound, comprising:
   presenting a plurality of different sound templates to a user from a series of tinnitus therapy sound templates;
   receiving a selection by the user of one or more of the templates;
   receiving an adjustment to one or more of the selected templates, wherein receiving the adjustment to one or more of the selected templates includes receiving a white noise edge enhancement adjustment having an intensity level based on an edge enhancement intensity input; and
   generating a therapy sound based on the adjusted selections including based on the received white noise edge enhancement adjustment.

2. The method of claim 1, wherein receiving the adjustment to one or more of the selected templates includes receiving an adjustment of one or more of a frequency, intensity, reverberation, timbre, Q factor, and vibrato for each of the one or more selected templates.

3. The method of claim 2, wherein the timbre adjustment includes one or more of an octave adjustment and a harmonic adjustment.

4. The method of claim 1, wherein the series of tinnitus therapy sound templates includes pre-defined tinnitus therapy sound templates, the method further comprising adjusting the pre-defined tinnitus therapy sound templates based on hearing threshold data from a patient audiogram, the hearing threshold data including one or more of decibel and frequency data.

5. The method of claim 1, wherein the series of tinnitus therapy sound templates includes a white noise, pink noise, pure tone, broad band noise, a cricket noise, an amplitude modulated sine wave, and a combined sound template.

6. A method for creating a tinnitus therapy, comprising:
   presenting each of a white noise, a pure tone, and a combined tone tinnitus therapy sound template to a user;
   adjusting the tinnitus therapy sound based on at least one of a frequency parameter and an intensity parameter selected by the user;
   adjusting the tinnitus therapy sound first based on the frequency parameter, second based on the intensity parameter, third based on one or more timbre inputs, the one or more timbre inputs including one or more of an octave input and a harmonic input, fourth based on a reverberation input, and fifth based on an edge enhancement input when the tinnitus therapy sound template selected by the user is the pure tone tinnitus therapy sound template; and
   generating a tinnitus therapy sound based on the tinnitus therapy sound template selected by the user including based on the adjusted tinnitus therapy sound.

7. The method of claim 6, wherein the presenting includes presenting each of the white noise, pure tone, and combined tone tinnitus therapy sound template to the user sequentially in a specified order.

8. The method of claim 6, wherein the presenting includes presenting each of the white noise, pure tone, and combined tone tinnitus therapy sound template to the user at different times and in groups by sound type.

9. The method of claim 6, wherein adjusting the tinnitus therapy sound based on the intensity parameter includes separately adjusting a right ear input and a left ear input intensity of the tinnitus therapy sound.

10. The method of claim 6, further comprising presenting each of a pink noise, a broad band noise, an amplitude modulated sine wave, and a cricket noise tinnitus therapy sound template to the user and further comprising adjusting the tinnitus therapy sound first based on the intensity parameter and second based on the reverberation input when the tinnitus therapy sound template selected by the user is one of the white noise tinnitus therapy sound template or the pink noise tinnitus therapy sound template.

11. The method of claim 10, further comprising adjusting the tinnitus therapy sound first based on the frequency parameter, second based on a Q factor input, third based on the intensity parameter, fourth based on the reverberation input, and fifth based on the edge enhancement input when the tinnitus therapy sound template selected by the user is the broad band noise tinnitus therapy sound template.

12. The method of claim 10, further comprising adjusting the tinnitus therapy sound first based on the frequency parameter, second based on the intensity parameter, third based on a vibrato input, fourth based on the reverberation input, and fifth based on the edge enhancement input when the tinnitus therapy sound template selected by the user is the cricket noise tinnitus therapy sound template.

13. A method for creating a tinnitus therapy, comprising:
   presenting each of a white noise, a pure tone, and a combined tone tinnitus therapy sound template to a user;
   adjusting the tinnitus therapy sound based on at least one of a frequency parameter and an intensity parameter selected by the user, wherein the combined tone tinnitus therapy template is a combined pure tone and broad band noise tinnitus therapy sound template and further comprising adjusting the tinnitus therapy sound first based on the frequency parameter, second based on a Q factor input, third based on the intensity parameter, fourth based on a timbre input, the timbre input including one or more of an octave input and a harmonic input, fifth based on a reverberation input, and sixth based on an edge enhancement input when the tinnitus therapy sound template selected by the user is the combined pure tone and broad band noise tinnitus therapy sound template; and
   generating a tinnitus therapy sound based on the tinnitus therapy sound template selected by the user including based on the adjusted tinnitus therapy sound.

14. The method of claim 6, wherein the user includes one or more of a patient and a medical provider and further comprising continuously playing the adjusted tinnitus therapy sound without breaks and tracking intensity changes to the continuously played tinnitus therapy sound over time based on input from the patient.

* * * * *